US008715619B2

(12) United States Patent
Karsunky

(10) Patent No.: US 8,715,619 B2
(45) Date of Patent: May 6, 2014

(54) COMPOSITIONS AND METHODS FOR TREATING HAEMATOLOGICAL PROLIFERATIVE DISORDERS OF MYELOID ORIGIN

(71) Applicant: Cellerant Therapeutics, Inc., San Carlos, CA (US)

(72) Inventor: Holger Karsunky, Redwood City, CA (US)

(73) Assignee: Cellerant Therapeutics, Inc., San Carlos, CA (US)

( * ) Notice: Subject to any disclaimer, the term of this patent is extended or adjusted under 35 U.S.C. 154(b) by 0 days.

(21) Appl. No.: 13/764,492

(22) Filed: Feb. 11, 2013

(65) Prior Publication Data

US 2013/0216558 A1 Aug. 22, 2013

Related U.S. Application Data

(63) Continuation of application No. 12/934,120, filed as application No. PCT/US2009/038459 on Mar. 26, 2009.

(60) Provisional application No. 61/039,701, filed on Mar. 26, 2008.

(51) Int. Cl.
| | | |
|---|---|---|
| A61K 51/00 | (2006.01) | |
| A61K 39/00 | (2006.01) | |
| A61K 39/395 | (2006.01) | |
| A61K 38/00 | (2006.01) | |
| G01N 33/00 | (2006.01) | |

(52) U.S. Cl.
USPC .......... 424/1.49; 424/173.1; 424/178.1; 424/134.1; 424/143.1; 424/142.1; 514/19.2; 435/7.24

(58) Field of Classification Search
None
See application file for complete search history.

(56) References Cited

U.S. PATENT DOCUMENTS

| | | |
|---|---|---|
| 6,280,955 B1 | 8/2001 | Cao |
| 7,049,095 B2 | 5/2006 | Sims et al. |
| 7,285,634 B2 | 10/2007 | Sims et al. |
| 7,390,880 B2 | 6/2008 | Bednarik et al. |
| 8,187,596 B1 | 5/2012 | Chackerian et al. |

(Continued)

FOREIGN PATENT DOCUMENTS

| | | |
|---|---|---|
| GB | 2472856 A | 2/2011 |
| WO | 96/23067 A1 | 8/1996 |

(Continued)

OTHER PUBLICATIONS

Estrove et al. Inhibition of Acute Myelogenous Leukemia Blast Proliferation by Interleukin-1 (IL-1) Receptor Antagonist and Soluble IL-1 Receptors, Blood, vol. 79, No. 8 Apr. 15, 1992: pp. 1938-1945.*

(Continued)

*Primary Examiner* — Jim Ketter
*Assistant Examiner* — Reza Ghafoorian
(74) *Attorney, Agent, or Firm* — Kilpatrick Townsend & Stockton LLP

(57) ABSTRACT

The disclosure relates to methods and compositions effective in the diagnosis, prognosis and treatment of human hematopoietic cancers. In particular, the disclosure provides tumor-associated genes that encode for cytokine receptors that are differentially expressed in hematopoietic tumor cells of myeloid origin compared with other cells, e.g., normal stem cells.

18 Claims, 6 Drawing Sheets

(56) References Cited

U.S. PATENT DOCUMENTS

| | | | |
|---|---|---|---|
| 8,258,268 | B2 | 9/2012 | Wu et al. |
| 2005/0276812 | A1* | 12/2005 | Ebens et al. ............... 424/178.1 |
| 2006/0252073 | A1* | 11/2006 | Yilmaz et al. ..................... 435/6 |
| 2007/0292970 | A1 | 12/2007 | Dugas et al. |
| 2008/0280774 | A1 | 11/2008 | Burczynski et al. |
| 2009/0048161 | A1* | 2/2009 | Chemtob et al. ................. 514/12 |
| 2010/0190652 | A1 | 7/2010 | Nagalla et al. |
| 2011/0015090 | A1 | 1/2011 | Majeti et al. |
| 2011/0110852 | A1 | 5/2011 | Miller et al. |
| 2011/0245090 | A1 | 10/2011 | Abbas et al. |
| 2012/0195900 | A1 | 8/2012 | Ghayur et al. |
| 2012/0201746 | A1 | 8/2012 | Liu et al. |
| 2012/0207752 | A1 | 8/2012 | Chackerian et al. |
| 2012/0225059 | A1 | 9/2012 | Fioretos et al. |

FOREIGN PATENT DOCUMENTS

| | | |
|---|---|---|
| WO | 2006/110593 A2 | 10/2006 |
| WO | 2009/091547 A1 | 7/2009 |
| WO | 2012/098407 A1 | 7/2012 |
| WO | 2012/142391 A1 | 10/2012 |
| WO | 2012/177595 A1 | 12/2012 |
| WO | 2013/023015 A2 | 2/2013 |

OTHER PUBLICATIONS

Anderson et al.; "Promotion of tissue inflammation by the immune receptor Tim-3 expressed on innate immune cells"; *Science*; 318:1141-1143 (2007).

Belkin et al.; "Killer cell Ig-like receptor and leukocyte Ig-like receptor transgenic mice exhibit tissue- and cell-specific transgene expression"; *J. Immunol.*; 171(6):3056-3063 (Sep. 2003).

Bennett et al.; "The myelodysplastic syndromes: Diagnosis, molecular biology and risk assessment"; *Hematology*; 10(Suppl 1):258-269 (2005).

Burgstaller, S. et al.; "The severity of FIPILI-PDGFRA-positive chronic eosinophilic leukaemia is associated with polymorphic variation at the IL5RA locus"; 2007, *Leukemia*, vol. 21, No. 12, pp. 2428-2432.

Chen, P.M. et al.; Insulin receptors on leukemia and lymphoma cells; 1983, *Blood*, vol. 62, No. 2, pp. 251-255.

Cho, R.W. et al.; "Recent advances in cancer stem cells"; 2008, *Genetics and Development*, vol. 18, pp. 48-53.

Debinski, W. et al.; "Molecular expression analysis of restrictive receptor for interleukin 13, a brain tumor-associated cancer/testis antigen"; 2000, *Molecular Medicine*, vol. 6, No. 5, pp. 440-449.

Dohner et al.; "Diagnosis and management of acute myeloid leukemia in adults: recommendations from an international expert panel, on behalf of the European LeukemiaNet"; *Blood*; 115:453-474 (2010) ePub on Oct. 30, 2009.

eBioscience website; "Hematopoietic Stem Cells"; n.d. (2 pages) retrieved on Feb. 16, 2012 from ebioscience.com/knowledgecenter/cell-type/hematopoietic-stem-cells.htm.

Funatsu et al.; "Characterization of a Novel Rat Brain Glycosylphosphatidylinositol-anchored Protein (Kilon), a Member of the IgLON Cell Adhesion Molecule Family", *J. Biol. Chem.*; 274(12):8224-8230 (Mar. 1999).

Gal, H. et al.; "Gene expression profiles of AML derived stem cells: similarity to hematopoietic stem cells"; 2006, *Leukemia*, vol. 20, No. 12, pp. 2147-2154.

Ginsburg et al.; "Personalized medicine: revolutionizing drug discover and patient care"; *Trends in Biotechnology*; 19(12):491-496 (Dec. 2001).

Giron-Michel, J. et al.; "Direct signal transduction via functional interferon-alphabeta receptors in CD34+ hematopoietic stem cells"; 2002, *Leukemia*, vol. 16, No. 6, pp. 1135-1142.

Gou, S. et al.; "Establishment of clonal colony-forming assay for propagation of pancreatic cancer cells with stem cell properties"; 2007, *Pancreas*, vol. 34, No. 4, pp. 429-435.

Hadidi et al.; "Preparation and functional properties of polyclonal and monoclonal antibodies to murine MD-1"; *Immunol. Lett.*: 77(2):97-103 (Jun. 2001).

Juric, D. et al.; "Differential gene expression patterns and interaction networks in BCR-ABL-positive and -negative adult acute lymphoblastic leukemias"; 2007, *Journal of Clinical Oncology*, vol. 25, No. 11, pp. 1341-1349.

Kaplan, G.C. et al.; "Insulin receptor overexpression in a human pre-B acute lymphocytic leukemia cell line with a t(1;19) chromosome translocation near the INSR locus"; 1989, *Biochemical Biophysical Research Communication*, vol. 159, No. 3, pp. 1275-1282.

Kornmann, M. et al.; "Pancreatic cancer cells express interleukin-13 and -4 receptors, and their growth is inhibited by *Pseudomonas* exotoxin coupled to interleukin-13 and -4"; 1999, *Anticancer Research*, vol. 19, No. 1A, pp. 125-131.

Krause et al.; "Characterization of MAX.3 antigen, a glycoprotein expressed on mature macrophages, dendritic cells and blood platelets : identity with CD84"; *Biochem. J.*; 346:729-736 (Mar. 2000).

Krause, S. et al.; "Blockade of interleukin-13-mediated cell activation by a novel inhibitory antibody to human IL-13 receptor alapha 1"; 2005, *Molecular Immunology*, vol. 43, No. 11, pp. 1799-1807.

Larramendy, M.L. et al.; "Overexpression of translocation-associated fusion genes of FGFR1, MYC, NPM1, and DEK, but absence of the translocations in acute myeloid leukemia. A microarray analysis"; 2002, *Haematologica*, vol. 87, No. 6, pp. 569-577.

Legare, R.D. et al.; "CBFA2, frequently rearranged in leukemia, is not responsible for a familial leukemia syndrome"; 1997, *Leukemia*, vol. 11, No. 12, pp. 2111-2119.

Levis et al.; "Internal tandem duplications of the FLT3 gene are present in leukemia stem cells"; *Blood*; 106(2):673-680 (Jul. 2005) ePub Mar. 29, 2005.

Maru, Y. et al.; "Human Itk: gene structure and preferential expression in human leukemic cells"; 1990, *Oncogene Research*, vol. 5, No. 3, pp. 199-204.

Miura et al.; "RP105 is associated with MD-1 and transmits an activation signal in human B cells"; *Blood*; 92(8):2815-2822 (Oct. 1998).

Nakajima et al.; "Cutting Edge: Human Myeloid Cells Express an Activating ILT Receptor (ILT1) That Associates with Fc Receptor γ-Chain"; *J. Immunol.*; 162(1):5-8 (Jan. 1999).

Nakayama et al.; "Tim-3 mediates phagocytosis of apoptotic cells and cross-presentation"; *Blood*; 113:3821-3830 (2009).

Pierce, A. et al.; "Ectopic interleukin-5 receptor expression promotes proliferation without development in a multipotent hematopoietic cell line"; 1998, *Journal of Cell Science*, vol. 111, No. 6, pp. 815-823.

Ramaswamy et al.; "DNA Microarrays in Clinical Oncology"; *J. Clin. Oncol.*; 20(7):1932-1941 (Apr. 2002).

Riccioni, R. et al.; "Interleukin (IL)-3/granulocyte macrophage-colony stimulating factor/IL-5 receptor alpha and beta chains are preferentially expressed in acute myeloid leukaemias with mutated FMS-related tyrosine kinase 3 receptor"; 2008, *British Journal of Haematology*, vol. 144, No. 3, pp. 376-387.

Schmitt et al.; "Quantitative expression of Toll-like receptor-2, -4, and -9 in dendritic cells generated from blasts of patients with acute myeloid leukemia"; *Transfusion*; 48(5):861-870 (Jan. 2008).

Sui et al.; "Human membrane protein Tim-3 facilitates hepatitis A virus entry into target cells"; *Int. J. Mol. Med.*; 17(6):1093-1099 (Jun. 2006).

Tefferi et al.; "Myeloproliferative neoplasms: contemporary diagnosis using histology and genetics"; *Nat. Rev. Clin. Oncol.*; 6:627-637 (2009).

Tomasson, M.H. et al.; "Somatic mutations and germline sequence variants in the expressed tyrosine kinase genes of patients with de novo acute myeloid leukemia"; 2008, *Blood*, vol. 111, pp. 4797-4808.

Tsuchiya, T. et al.; "Th1, Th2, and activated T-cell marker and clinical prognosis in peripheral T-cell lymphoma, unspecified: comparison with AILD, ALCL, lymphoblastic lymphoma, and ATLL"; 2003, *Blood*, vol. 103, No. 1, pp. 236-241.

Tyner, J.W. et al.; "RNAi screening of the tyrosine kinome identifies therapeutic targets in acute myeloid leukemia"; 2007, *Blood*, vol. 111, pp. 2238-2245.

(56) References Cited

OTHER PUBLICATIONS

Wang et al.; "Treatment of acute myeloid leukemia by directly targeting both leukemia stem cells and oncogenic molecule with specific scFv-immunolipoplexes as a deliverer"; *Medical Hypotheses*; 70:122-127 (2008).

Yalcintepe, L. et al.; "Expression of interleukin-3 receptor subunits on defined subpopulations of acute myeloid leukemia blasts predicts the cytotoxicity of diphtheria toxin interleukin-3 fusion protein against malignant progenitors that engraft in immunodeficient mice"; 2006, *Blood*, vol. 108, No. 10, pp. 3530-3537.

Yoshida, K. et al.; "Studies on natural ST2 gene products in the human leukemic cell line UT-7 using monoclonal antihuman ST2 antibodies"; 1995, *Hybridoma*, vol. 14, No. 5, pp. 419-427.

The Supplementary European Search Report from EP Application No. 09726329.7, dated Feb. 2, 2012.

Office Action from U.S. Appl. No. 12/810,006 dated Jan. 28, 2013.
Office Action from U.S. Appl. No. 12/810,006 dated May 17, 2012.
Office Action from U.S. Appl. No. 12/934,120 dated Apr. 25, 2013.
Office Action from U.S. Appl. No. 12/934,120 dated Feb. 28, 2012.
Office Action from U.S. Appl. No. 12/934,120 dated Oct. 3, 2012.
U.S. Appl. No. 12/810,006, filed Sep. 13, 2010 (73 pages).
U.S. Appl. No. 12/934,120, filed Nov. 5, 2010 (80 pages).

Jan et al.; "Prospective separation of normal and leukemic stem cells based upon differential expression of TIM3, a human acute myeloid leukemia stem cell marker"; Proc. Natl. Acad. Sci. USA; 108(12):5009-25014 (2011).

Kikushige et al.; "TIM-3 as a therapeutic target for malignant stem cells in acute myelogenous leukemia"; *Ann. N.Y. Acad. Sci.*; 1266:118-123 (2012).

* cited by examiner

COMPOSITIONS AND METHODS FOR TREATING HAEMATOLOGICAL PROLIFERATIVE DISORDERS OF MYELOID ORIGIN

CROSS-REFERENCES TO RELATED APPLICATIONS

This application is a continuation of U.S. application Ser. No. 12/934,120, filed Nov. 5, 2010, which is the U.S. National Stage of International Application No. PCT/US2009/038459, filed Mar. 26, 2009, which claims the benefit of priority of U.S. Provisional Application No. 61/039,701, filed Mar. 26, 2008, each of which is incorporated herein by reference in its entirety.

BACKGROUND OF THE INVENTION

1. Technical Field

The present disclosure relates generally to agents capable of specifically targeting cancer stem cell markers and methods of using the agents, particularly in diagnostic and therapeutic treatments. In particular, the present disclosure provides cytokine receptors as novel cancer stem cell targets that are expressed extracellularly and that are targeted by antibodies and other agents disclosed herein.

2. Background

The cells of the hematopoietic system arise from multipotent progenitors, the hematopoietic stem cells (HSCs), which progress through a series of developmental programs to ultimately form the terminally differentiated cells of the myeloid or lymphoid lineage. It is believed that in the initial stages of hematopoiesis, HSCs commit to two distinguishable oligopotent but developmentally restricted progenitor cell types, the common lymphoid progenitors (CLPs) and the common myeloid progenitor (CMPs). T lymphocytes, B lymphocytes, natural killer (NK) cells, and lymphoid dendritic cells develop from corresponding progenitor cells derived from the CLPs whereas erythroid cells, megakaryocytes, granulocytes, macrophages, and myeloid dendritic cells develop from their corresponding progenitor cells derived from CMPs. Cell populations at each stage of differentiation are distinguishable from other cell populations in the hematopoietic pathway based on programmed expression of a unique set of cell markers.

Although HSCs are capable of self renewal—cell division that results in at least one of the daughter cells having the same characteristics as the parent cell—the progenitor cells committed to the lymphoid or myeloid lineages lose their potential to self-renew. That is, mitotic cell division of the committed progenitors leads to differentiated progeny rather than generation of a cell with the same proliferative and differentiation capacity as the parent cell. This loss of self-renewal potential is seen in the ability of committed progenitors cells to maintain hematopoiesis only for a limited time period (i.e., short term reconstitution) following transplantation of the progenitor cells into an immunocompromised animal, as compared to an HSC, which can completely regenerate and maintain hematopoiesis during the life of the host animal (i.e., long term reconstitution).

It has been observed, however, that in certain disease states of the hematopoietic system, dysregulation of cellular regulatory pathways may lead to progenitor cells that acquire the ability to self-renew. For instance, acute myeloid leukemia (AML, also called acute myelogenous leukemia) is a myeloproliferative disorder marked, in part, by infiltration of bone marrow by abnormal hematopoietic cells. Indeed, the stem cell nature of cancer was first shown in AML (Lapidot et al., 1994 Nature 17:645-8). AML is categorized into different subtypes based on morphological features and cytochemical staining properties, and although the self-renewal characteristic in most types of AML is attributable to leukemic cells having cell marker phenotypes consistent with HSCs (Bonnet, D. and Dick, J. E., Nat. Med. 3(7):730-737 (1997)), the chromosomal abnormality associated with the AML M3 subtype is observed in cell populations with a cell marker phenotype characteristic of more differentiated cells of the myeloid lineage ($CD34^-$, $CD38^+$) whereas the HSC population in M3 does not carry the translocation (Turhan, A. G. et al., Blood 79:2154-2161 (1995)).

Gain of self-renewing characteristic in the committed progenitor cell population is also suggested in chronic myeloid leukemia (CML, also called chronic myelogenous leukemia, or chronic granulocytic leukemia), a disease commonly associated with the Philadelphia chromosome, which is a balanced translocation between chromosomes 9 and 22, t(9;22). The translocation produces a fusion between the bcr and c-abl genes and results in expression of a chimeric protein BCR-ABL with increased tyrosine kinase activity. Although the HSC population in CML typically contains the chromosomal abnormality, the BCR-ABL fusion protein is mainly expressed in the committed cells of myelomonocytic lineage rather than the HSCs, indicating that committed cells in the myeloid lineage may be the source of the leukemic cells rather than the HSCs. Additional evidence for the committed myeloid cells as being the source of the leukemic clones in CML comes from studies of controlled expression of BCR-ABL in transgenic animals. Use of promoters active specifically in myeloid progenitor cells to force expression of BCR-ABL in committed cells but not in HSCs produces disease characteristic of CML in these transgenic animal models (Jaiswal, S. et al., Proc. Natl. Acad. Sci. USA 100:10002-10007 (2003)).

Although myeloproliferative disorders, such as AML and CML are typically associated with cytogenetic abnormalities, the cytogenetic defect may not be solely responsible for the proliferative trait. In some instances, the chromosomal abnormality is observed in normal cells, which suggests that accumulation of additional mutations in either the HSCs or committed myeloid cells is required for full manifestation of the disease state. Even in CML, the disorder displays a multiphasic course, beginning from a chronic phase, which after 3-5 years and up to 10 years, leads to an accelerated or blastic phase similar to AML. The time period required to transition from the chronic phase (less than 5% blasts or promyelocytes) to the blastic phase (>30% blasts in the peripheral blood or bone marrow) may reflect the time needed to accumulate the mutations responsible for conversion of the chronic phase to the more aggressive blastic phase. For the most part, however, the leukemic cells appear to retain the cell marker phenotypes detectable in normal progenitor cells.

Treatments for proliferative disorders normally rely on the sensitivity of proliferating cells to cytotoxic or cytostatic chemotherapeutic agents. For instance, busulfan, a bifunctional alkylating agent, and hydroxyurea, an inhibitor of ribonucleoside diphosphate, affect DNA synthesis and stability, resulting in toxicity to dividing cells. Other therapeutic agents of similar activity include cytosine arabinoside (cytarabine) and daunorubicin. However, the effects of these agents are non-discriminatory and as a result they have serious side effects due to toxicity to normal dividing cells.

Another treatment used in patients with haematological malignancies is bone marrow transplant (BMT), where the recipient's hematopoietic cells are eliminated with radiation and/or chemotherapy (e.g., cyclophosphamide), and the hematopoietic system reconstituted by transplant of healthy hematopoietic stem cells. Typically, the transplant uses HLA matched allogeneic bone marrow cells from a family member (HLA-identical) or a serologically matched altruistic donor (MUD). Approximately, <50% of recipients find a donor, with exactly matching histocompatibility. Transplant with less well matched donors marketed increases the transplant related morbidity and mortality. This therapeutic approach has limited application because of its dependence on the availability of suitable donors and because the treatments show better outcome for patients in the chronic or early phase of the disease as compared to acute or late stages.

Antibody therapy for cancer involves the use of antibodies, or antibody fragments, against an antigen to target antigen-expressing tumor cells. Because antibody therapy targets cells expressing a particular antigen, there is a possibility of cross-reactivity with normal cells and can lead to detrimental results. Substantial efforts have been directed to finding tumor-specific antigens. Tumor-specific antigens are found almost exclusively on tumors or are expressed at a greater level in tumor cells than the corresponding normal cells. Thus, tumor-specific antigens provide targets for antibody targeting of cancer, or other disease-related, cells expressing the antigen, as well as providing markers for diagnosis, for example, by identifying increased levels of expression. In immunotherapy approaches, antibodies specific to such tumor-specific antigens can be conjugated to cytotoxic compounds or can be used alone in immunotherapy.

Immunotherapy as a treatment option against hematopoietic cancers, such as AML, is limited by the lack of tumor-associated antigens that are tumor-specific and that are shared among diverse patients. It is desirable to find other therapeutic agents that take advantage of the developmental origins of the leukemic cells by exploiting the common characteristics between leukemic cells and normal cell populations in the myeloid lineage. This approach would provide treatments that can supplement traditional therapies for myeloid leukemias, or that can be used as an alternative treatment to directly target the stem cell fractions of leukemic cells. This approach also provides additional diagnostic and prognostic strategies, as well as strategies for monitoring the efficacy of a therapeutic regimen.

Generally, therapeutic treatment is more effective when tailored to a specific type of hematopoietic cancer. Predicting and determining efficacy of a treatment regime over time is also valuable in terms of clinical management. It is thus desirable to find tumor-specific markers that can be used in more efficient and accurate diagnosis and prognosis of myelioid leukemic disorders, such as AML.

Cytokine receptors belong to families of receptor proteins, which are divided into two subsets on the basis of the presence or absence of particular sequence motifs. The two subsets are the hematopoietin-receptor family (also referred to as the class I cytokine receptor family) and the class II cytokine receptor superfamily (many of which are receptors for interferons or interferon-like cytokines). In the hematopoietin-receptor family, the α chain often defines ligand specificity of the receptor and the β or γ chain initiates intracellular signaling.

BRIEF SUMMARY OF THE INVENTION

The present invention provides methods and compositions effective in the diagnosis and treatment of human hematopoietic cancers of myeloid origin. As described herein, the following cytokine receptor markers have been found to be associated with hematopoietic tumor cells (HTCs) of myeloid origin: colony stimulating factor 1 receptor (CSF1R); interleukin 13 receptor, alpha 1 (IL13RA1); interleukin 1 receptor accessory protein (IL1RAP); interferon-a receptor 1 (IFNAR1); interleukin-5 receptor alpha (IL5RA); insulin receptor (INSR); interleukin 1 receptor-like 1 (IL1RL1); leukocyte receptor tyrosine (LTK); and tumor associated calcium signal transducer 1 (TACSTD1).

In preferred embodiments, the disclosed cytokine receptor markers are differentially expressed in HTCs of myeloid origin compared to normal HSCs. In some embodiments, the disclosed cytokine receptor markers are differentially expressed by at least about 2 fold. In other embodiments, the cytokine receptor markers are differentially expressed by at least about 3 fold. In other embodiments, the cytokine receptor markers are differentially expressed by at least about 5 fold, etc. The present disclosure provides agents specifically directed to these markers that find use in therapeutic and diagnostic applications.

The following cytokine receptor markers are over-expressed on the surface of myelogenous HTCs: colony stimulating factor 1 receptor (CSF1R); interleukin 13 receptor, alpha 1 (IL13RA1); interleukin 1 receptor accessory protein (IL1RAP); interferon-a receptor 1 (IFNAR1); interleukin-5 receptor alpha (IL5RA); insulin receptor (INSR); interleukin 1 receptor-like 1 (IL1RL1); leukocyte receptor tyrosine (LTK); and tumor associated calcium signal transducer 1 (TACSTD1). Agents specifically directed to these markers can specifically bind HTCs of myeloid origin by virtue of binding to the surface-expressed marker.

Compositions that specifically target the disclosed myelogenous HTC markers (e.g., the cytokine receptors disclosed herein), interfering with the expression thereof or binding to the expressed products, are provided herein, as well as methods of using the same in the diagnosis, prognosis and treatment of haematological proliferative disorders characterized by such markers. The compositions include antibodies that specifically bind one or more of the extracellularly-expressed antigens associated with myelogenous HTCs that can inhibit their proliferation and/or mediate their destruction. The invention further provides immortal cell lines that produce one or more such antibodies.

In one aspect, the invention provides antibodies that specifically bind to one or more of colony stimulating factor 1 receptor (CSF1R); interleukin 13 receptor, alpha 1 (IL13RA1); interleukin 1 receptor accessory protein (IL1RAP); interferon-a receptor 1 (IFNAR1); interleukin-5 receptor alpha (IL5RA); insulin receptor (INSR); interleukin 1 receptor-like 1 (IL1RL1); leukocyte receptor tyrosine (LTK); and tumor associated calcium signal transducer 1 (TACSTD1) associated with HTCs of myeloid origin. In some embodiments, the antibody is a monoclonal antibody, for example, an antibody which is produced from a hybridoma cell line. In preferred embodiments, the monoclonal antibody specifically binds to hematopoietic tumor cells of myeloid origin including, without limitation, chronic myeloid leukemia (CML) blasts, acute myeloid leukemia (AML) blasts, as well as to cells from the KG-1a, Pfeiffer, MOLT-3, GA-10, Ramos, and Jurkat cell lines. In another embodiment, the monoclonal antibody specifically binds to AML blasts.

In preferred embodiments, the invention provides antibodies that specifically bind to one or more of the disclosed cytokine receptors associated with myelogenous HTCs and thereby inhibit their proliferation and/or mediate their destruction, but do not mediate destruction of normal hematopoietic stems cells. In a preferred embodiment, the antibody is a monoclonal antibody. In some embodiments, the antibody is an IgG isotype or a humanized antibody. In one embodiment, the humanized antibody is from a transgenic animal that includes a human immunoglobulin gene.

In another embodiment, the invention provides an antibody complex having at least one antibody that specifically binds to one or more of the disclosed cytokine receptors associated with HTCs of myeloid origin. In a preferred embodiment, the antibody complex comprises a multimer comprising a monoclonal antibody that binds to one of the disclosed cytokine receptors.

In alternative embodiments, the antibodies of the present invention include detectable moieties, radioactive compounds (e.g. radioisotopes or radionuclides), or bioactive compounds (e.g. drugs or small molecules). In some embodiments, the bioactive compound is a cytotoxic agent.

In another embodiment, the invention provides small molecules, which bind, preferably specifically, to one or more of the cytokine receptor polypeptides disclosed herein. In preferred embodiments, the small molecule is a small organic molecule, including small organic molecules known in the art as being an agonist or antagonist of a polypeptide corresponding to a cytokine receptor disclosed herein. Small molecules known to bind polypeptides corresponding to other cytokine receptors disclosed herein can also find use in the subject therapeutic, prognostic and/or diagnostic applications.

Optionally, the small molecule is conjugated to a growth inhibitory agent or cytotoxic agent such as a toxin, including, for example, a maytansinoid or calicheamicin, an antibiotic, a radioactive isotope, a nucleolytic enzyme, or the like. The small molecules that find use in the therapeutic methods of the instant invention preferably induce death of a cell to which they bind. For diagnostic purposes, the small molecules can be detectably labeled and/or attached to a solid support.

The subject agents and antibodies directed to the disclosed cytokine receptors have significant therapeutic and diagnostic utilities and in additional aspects pharmaceutical compositions, methods and kits are provided employing the subject agents and antibodies for use in diagnosing and treating haematological proliferative disorders characterized by the presence of one or more of the disclosed cytokine receptors such as, e.g., acute myelogenous leukemia, acute myelomonocytic leukemia, chronic myelogenous leukemia and acute myeloid leukemia.

In one aspect, the present disclosure provides methods of using antibodies to target one or more of the disclosed cytokine receptors. In the present teachings, the antibodies provide a basis for immunotherapeutic approaches in treating disorders involving hematopoietic tumor cells (HTCs) of myeloid origin, for example, myeloproliferative disorders such as chronic myeloid leukemia (CML) and acute myeloid leukemia (AML).

In one embodiment, the present invention provides methods of inhibiting the proliferation of HTCs of myeloid orign by contacting the HTCs with a composition comprising an antibody or other agent directed to one or more of the disclosed cytokine receptors. In another embodiment, the present invention provides methods of mediating the destruction of HTCs of myeloid origin by contacting the HTCs with a composition comprising an antibody or other agent directed to one or more of the disclosed cytokine receptors. In one embodiment, the antibody is a monoclonal antibody that specifically binds an epitope on a disclosed cytokine receptor or a portion thereof. In another embodiment, the composition comprises an antibody complex.

In another embodiment, a method of depleting HTCs over-expressing one or more of the disclosed cytokine receptors in a subject in need thereof is provided in which the subject is administered a composition comprising an antibody or antibody complex as described herein. In yet another embodiment, the present invention provides a method of treating a patient with a myelogenous haematological proliferative disorder characterized by over-expression in HTCs of one or more of the disclosed cytokine receptors where the patient is administered a composition that includes an antibody or antibody complex or other agent as described herein.

In some embodiments, the methods of the present invention are suitable for treating a haematological proliferative disorder of myeloid orgin, including myoproliferative disorders such as, for example, chronic myeloid leukemia (CML) and/or acute myeloid leukemia (AML).

In another aspect, the present invention provides diagnostic methods for hematological proliferative disorders of myeloid origin, where the level of an expression product corresponding to one or more of the disclosed cytokine receptors is detected. In one embodiment, the expression product is a transcription product, such as RNA. Methods of detecting the level of RNA include utilizing a specific hybridization probe or an array of such probes. In another embodiment, the expression product is a translation product such as one or more of the cytokine receptor antigens corresponding to one or more of the cytokine receptors disclosed herein. Methods of detecting the level of an antigen include utilizing antibodies of the instant disclosure. The RNA or antigen level can be compared to control levels, e.g., levels obtained from samples of normal HSCs.

In another embodiment, the present invention provides prognostic methods for predicting the efficacy of treating a haematological proliferative disorder of myeloid origin, where the level of an expression product corresponding to one or more of the disclosed cytokine receptors is detected and wherein the expression product level is correlated with a treatment outcome. In one embodiment, the expression product is RNA and lower expression levels correlate with more favorable outcomes.

In still another embodiment the present invention provides methods for monitoring the efficacy of treating a haematological proliferative disorder of myeloid origin, where the level of an expression product corresponding to one or more of the disclosed cytokine receptors is detected at various time points; and where a change in the level is correlated with treatment outcome. In one embodiment, the expression product is RNA and decreasing levels indicate a positive response to treatment.

In some embodiments, the methods of the present invention are suitable for diagnosis, prognosis and monitoring of a haematological proliferative disorder of myeloid origin, such as myoproliferative disorders. The present invention provides methods of diagnosis, prognosis and monitoring of chronic myeloid leukemia (CML) and/or acute myeloid leukemia (AML). In a particularly preferred embodiment, the haematological proliferative disorder is AML and the level of RNA or antigen is detected using a test sample comprising AML HTCs, which is compared to control levels obtained from a control sample of normal HSCs.

DETAILED DESCRIPTION OF THE INVENTION

5.1 Definitions

Figure 1:
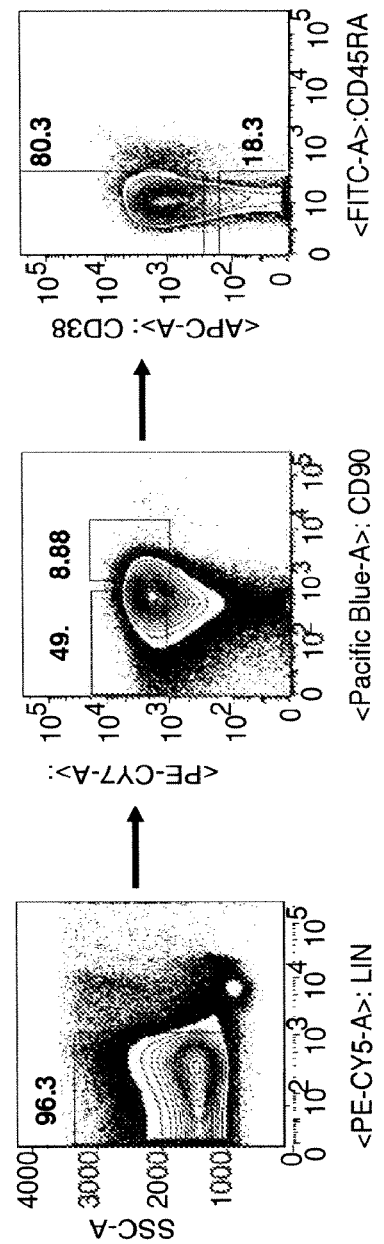
FIG. 1 shows the results of double sorting Lin$^-$CD34$^+$CD90$^+$CD45RA$^-$CD38$^-$ and Lin$^-$CD34$^+$CD90$^+$CD45RA$^-$CD38$^+$ cells from 3 samples taken from 3 individual mobilized peripheral blood (MPB) donors that are not afflicted with AML.

For the following descriptions, the technical and scientific terms used herein will have the meanings commonly understood by one of ordinary skill in the art, unless specifically defined otherwise. Accordingly, the following terms are intended to have the following meanings:

The terms "cancer stem cell (CSC) markers" or "cancer stem cell (CSC) targets" as well as "hematopoietic tumor cell (HTC) markers" or "hematopoietic tumor cell (HTC) targets" refer to genes and their expression products, such as mRNA and polypeptides, that have been found to be associated with HTCs by virture, for example, of increased expression and/or biological activity. For example, in the case of the CSF1R marker disclosed herein, CSF1R mRNA transcribed from the CSF1R gene is found at higher levels in samples comprising AML HTCs as compared with samples comprising normal HSCs. An HTC associated with a given marker is referred to herein as a "marker+ HTC."

"HTCs of myeloid origin" particularly refers to cancer stem cells derived from cells of the myeloid (nonlymphoid) lineages, including monocytes, macrophages, neutrophils, basophils, eosinophils, erythrocytes, megakaryocytes/platelets, dendritic cells and the like. HTCs of myeloid origin will be those found in myeloid leukemias, such as AML and CML, where it is believed that progenitor cells committed to myeloid lineages regain self-renewing characteristics. Various forms of leukemia, for example, appear to have their origins in a small population of HSCs or committed myeloid progenitor cells in which the cells acquire a combination of mutations that give rise to the malignant phenotype. The terms "HTCs of myeloid origin" and "myeloid HTCs" or "myelogenous HTCs" are used herein interchangeably.

"Hematopoietic stem cell" or "HSC" generally refers to clonogenic, self renewing pluripotent cells, capable of ultimately differentiating into all cell types of the hematopoietic system, including B cells T cells, NK cells, lymphoid dendritic cells, myeloid dendritic cells, granulocytes, macrophages, megakaryocytes, and erythroid cells. As with other cells of the hematopoietic system, HSCs are typically defined by the presence of a characteristic set of cell markers.

"Marker phenotyping" refers to identification of markers or antigens on cells for determining its phenotype (e.g., differentiation state and/or cell type). This may be done by immunophenotyping, which uses antibodies that recognize antigens present on a cell. The antibodies may be monoclonal or polyclonal, but are generally chosen to have minimal cross-reactivity with other cell markers. It is to be understood that certain cell differentiation or cell surface markers are unique to the animal species from which the cells are derived, while other cell markers will be common between species. These markers defining equivalent cell types between species are given the same marker identification even though there are species differences in structure (e.g., amino acid sequence). Cell markers include cell surfaces molecules, also referred to in certain situations as cell differentiation (CD) markers, and gene expression markers. The gene expression markers are those sets of expressed genes indicative of the cell type or differentiation state. In part, the gene expression profile will reflect the cell surface markers, although they may include non-cell surface molecules.

Lineage markers are cell surface antigens that can be used for immunophenotyping cells of a particular developmental lineage. For example, a set of 'Lin' antigens comprising CD2, CD3, CD4, CD5, CD8, NK1.1, B220, TER-119, Gr-1 can be used to identify mature murine blood cells. Cells that do not express these marker antigens, or express them at very low levels, are said to be lineage marker negative (Lin). The monoclonal antibody cocktails directed against these lineage markers can be used to remove cells expressing these antigens from source tissues (for example, bone marrow, umbilical cord blood, mobilized peripheral blood, fetal liver, and the like). This negative selection procedure yields a population of cells that is enriched for primitive hematopoietic stem cells or very early progenitor cells or precursor cells that do (not yet) express these markers (see, for example: KTLS cells). These cells are called lineage negative cells, abbreviated "Lin" cells. Several subpopulations of lineage negative cells have been identified that are enriched for hematopoietic stem cells. They include Lin$^-$CD34$^+$ cells (Krause et al, 1994), Lin$^-$Sca$^{-1+}$c-Kit$^+$Thy1$^{low}$ cells (Fleming et al, 1993) and human CD34$^+$ CD38$^-$ cell populations.

"Agent" refers to any molecule specifically directed to one or more of the disclosed HTC markers and that can act to inhibit, hinder and/or suppress a biological activity of the HTC marker in a haematological proliferative disorder and/or to mediate destruction of the HTCs. Agents include any molecule that specifically interacts with an HTC marker gene and/or expression product, including for example, antibodies that specifically bind to an antigen corresponding to a HTC marker to inhibit HTC proliferation and/or mediate their destruction; antisense molecules that interfere with the expression of an HTC marker; or molecules that interfere with a biological activity mediated by the HTC marker, such as by sterically inhibiting interaction between an HTC marker and its ligand to interfere with activation of a cancer stem cell signal transduction pathway. The molecule may be one known in the art, e.g., small molecule agonists or antagonists directed towards one or more of the HTC markers disclosed herein. An antibody that specifically binds to an antigen corresponding to an HTC marker disclosed herein is referred to as a "marker specific antibody."

A "small molecule", "small molecule compound", or "small organic molecule" refers to a molecule having a molecular weight usually less than about 2000 daltons, alternatively less than about 1500, about 750, about 500, about 250 or about 200 daltons in size, wherein such molecules are known in the art to be capable of binding (preferably specifically binding) to a polypeptide corresponding to an cytokine receptor disclosed herein.

With regard to the binding of a small molecule compound to a target molecule, the term "specifically interacts with" or "specifically binds" or is "directed to or towards" a particular product means binding that is measurably different from a non-specific interaction. Specific binding can be measured, for example, by methods known in the art, e.g., using competition assays with a control molecule that is similar to the target, for example, an excess of non-labeled target. A small molecule compound that specifically binds a target can have a Kd for the target of at least about $10^{-4}$ M, alternatively at least about $10^{-5}$ M, alternatively at least about $10^{-6}$ M, alternatively at least about $10^{-7}$ M, alternatively at least about $10^{-8}$ M, alternatively at least about $10^{-9}$ M, alternatively at least about $10^{-10}$ M, alternatively at least about $10^{-11}$ M, alternatively at least about $10^{-12}$ M, or greater. In one embodiment, the term "specific binding" refers to binding where a small molecule compound binds to its particular target without substantially binding to any other polypeptide or macromolecule.

"Antibody" refers to a composition comprising a protein that binds specifically to a corresponding antigen and has a common, general structure of immunoglobulins. The term antibody specifically covers polyclonal antibodies, monoclonal antibodies, dimers, multimers, multispecific antibodies (e.g., bispecific antibodies), and antibody fragments, so long as they exhibit the desired biological activity. Antibodies may be murine, human, humanized, chimeric, or derived from other species. Typically, an antibody will comprise at least two heavy chains and two light chains interconnected by disulfide bonds, which when combined form a binding domain that interacts with an antigen. Each heavy chain is comprised of a heavy chain variable region ($V_H$) and a heavy chain constant region ($C_H$). The heavy chain constant region is comprised of three domains, $C_{H1}$, $C_{H2}$ and $C_{H3}$, and may be of the mu, delta, gamma, alpha or epsilon isotype. Similarly, the light chain is comprised of a light chain variable region ($V_L$) and a light chain constant region ($C_L$). The light chain constant region is comprised of one domain, $C_L$, which may be of the kappa or lambda isotype. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system. The heavy chain constant region mediates binding of the immunoglobulin to host tissue or host factors, particularly through cellular receptors such as the Fc receptors (e.g., FcγRI, FcγRII, FcγRIII, etc.). As used herein, antibody also includes an antigen binding portion of an immunoglobulin that retains the ability to bind antigen. These include, as examples, F(ab), a monovalent fragment of $V_L$ $C_L$ and $V_H$ $C_H$ antibody domains; and F(ab)$_2$ fragment, a bivalent fragment comprising two Fab fragments linked by a disulfide bridge at the hinge region. The term antibody also refers to recombinant single chain Fv fragments (scFv) and bispecific molecules such as, e.g., diabodies, triabodies, and tetrabodies (see, e.g., U.S. Pat. No. 5,844,094).

Antibodies may be produced and used in many forms, including antibody complexes. As used herein, the term "antibody complex" or "antibody complexes" is used to mean a complex of one or more antibodies with another antibody or with an antibody fragment or fragments, or a complex of two or more antibody fragments. Antibody complexes include multimeric forms of antibodies directed to the disclosed cytokine receptors such as homoconjugates and heteroconjugates as well as other cross-linked antibodies as described herein.

"Antigen" is to be construed broadly and refers to any molecule, composition, or particle that can bind specifically to an antibody. An antigen has one or more epitopes that interact with the antibody, although it does not necessarily induce production of that antibody.

The terms "cross-linked", "cross-linking" and grammatical equivalents thereof, refer to the attachment of two or more antibodies to form antibody complexes, and may also be referred to as multimerization. Cross-linking or multimerization includes the attachment of two or more of the same antibodies (e.g. homodimerization), as well as the attachment of two or more different antibodies (e.g. heterodimerization). Those of skill in the art will also recognize that cross-linking or multimerization is also referred to as forming antibody homoconjugates and antibody heteroconjugates. Such conjugates may involve the attachment of two or more monoclonal antibodies of the same clonal origin (homoconjugates) or the attachment of two or more antibodies of different clonal origin (also referred to as heteroconjugates or bispecific). Antibodies may be crosslinked by non-covalent or covalent attachment. Numerous techniques suitable for cross-linking will be appreciated by those of skill in the art. Non-covalent attachment may be achieved through the use of a secondary antibody that is specific to the primary antibody species. For example, a goat anti-mouse (GAM) secondary antibody may be used to cross-link a mouse monoclonal antibody. Covalent attachment may be achieved through the use of chemical cross-linkers.

"Epitope" refers to a determinant capable of specific binding to an antibody. Epitopes are chemical features generally present on surfaces of molecules and accessible to interaction with an antibody. Typical chemical features are amino acids and sugar moieties, having three-dimensional structural characteristics as well as chemical properties including charge, hydrophilicity, and lipophilicity. Conformational epitopes are distinguished from non-conformational epitopes by loss of reactivity with an antibody following a change in the spatial elements of the molecule without any change in the underlying chemical structure.

"Humanized antibody" refers to an immunoglobulin molecule containing a minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, a humanized antibody will comprise substantially all of at least one, and typically two, variable domains, in which all or substantially all of the CDR regions correspond to those of a non-human immunoglobulin and all or substantially all of the framework (FR) regions are those of a human immunoglobulin consensus sequence. A humanized antibody will also encompass immunoglobulins comprising at least a portion of an immunoglobulin constant region (Fc), generally that of a human immunoglobulin (Jones et al., Nature 321:522-525 (1986); Reichmann et al, Nature 332:323-329 (1988)).

"Immunogen" refers to a substance, compound, or composition which stimulates the production of an immune response.

The term "immunoglobulin locus" refers to a genetic element or set of linked genetic elements that comprise information that can be used by a B cell or B cell precursor to express an immunoglobulin peptide. This peptide can be a heavy chain peptide, a light chain peptide, or the fusion of a heavy and a light chain peptide. In the case of an unrearranged locus, the genetic elements are assembled by a B cell precursor to form the gene encoding an immunoglobulin peptide. In the case of a rearranged locus, a gene encoding an immunoglobulin peptide is contained within the locus.

"Isotype" refers to an antibody class defined by its heavy chain constant region. Heavy chains are generally classified as gamma, mu, alpha, delta, epsilon and designated as IgG, IgM, IgA, IgD, and IgE. Variations within each isotype are categorized into subtypes, for example subtypes of IgG are divided into $IgG_1$, $IgG_2$, $IgG_3$, and $IgG_4$, while IgA is divided into $IgA_1$ and $IgA_2$. The IgY isotype is specific to birds.

"Monoclonal antibody" or "monoclonal antibody composition" refers to a preparation of antibody molecules of single molecular composition. A monoclonal antibody composition displays a single binding specificity and affinity for a particular epitope.

The term "human monoclonal antibody" refers to antibodies displaying a single binding specificity which have variable and/or constant regions (if present) derived from human germline immunoglobulin sequences. In one embodiment, the human monoclonal antibodies are produced by a hybridoma which includes a B cell obtained from a transgenic non-human animal, e.g., a transgenic mouse, having a genome comprising a human heavy chain transgene and a light chain transgene fused to an immortalized cell.

"Single chain Fv" or "scFv" refers to an antibody comprising the $V_H$ and $V_L$ regions of an antibody, wherein these domains are present in a single polypeptide chain. Generally, a scFv further comprises a polypeptide linker between the $V_H$ and $V_L$ domains which enables the scFv to form the desired structure for antigen binding.

"Specifically immunoreactive" or antibody that "specifically binds" refers to a binding reaction of the antibody that is determinative of the presence of the antigen in a heterogeneous population of antigens. The antibody may be described as being "directed to" or "directed against" the particular antigen. Under a designated immunoassay condition, the antibody binds to the antigen at least two times, and typically 10-1000 times or more over background. "Specifically immunoreactive" or "antibody that specifically binds" also refers to an antibody that is capable of binding to an antigen with sufficient affinity such that the antibody is useful in targeting a cell having the antigen bound to its surface or in targeting the soluble antigen itself. In such embodiments, the extent of non-specific binding is the amount of binding at or below background and will typically be less than about 10%, preferably less than about 5%, and more preferably less than about 1% as determined by fluorescence activated cell sorting (FACS) analysis or radioimmunoprecipitation (RIA), for example.

"Recombinant antibody" refers to all antibodies prepared and expressed, created or isolated by recombinant techniques. These include antibodies obtained from an animal that is transgenic for the immunoglobulin locus, antibodies expressed from a recombinant expression vector, or antibodies created, prepared, and expressed by splicing of any immunoglobulin gene sequence to other nucleic acid sequences.

The term "associated with" as in, for example, cytokine receptor markers being "associated with" hematopoietic tumor cells (HTCs), refers to the case where the HTC marker genes (e.g., the cytokine receptor genes) are expressed at differential levels in HTCs as opposed to other mammalian cells, e.g., normal HSCs. That is, a transcription product, such as RNA, and/or a translation product, such as a polypeptide, corresponding to the cytokine receptor gene has been found at differential levels in one or more samples comprising HTCs compared with one or more samples comprising other mammalian cells, e.g., normal HSCs.

"Expression" or "expressing" as used herein refers to both transcriptional and translational processes directed by a gene. That is, the terms refer to the process of converting genetic information encoded in a nucleic acid sequence (gene) into RNA (e.g., mRNA rRNA, tRNA, snRNA, etc.) through transcription of the gene; and/or converting genetic information into protein through translation of mRNA. Similarly, "expression product" as used herein refers to a transcription or translation product of a gene, and includes, e.g., RNA (mRNA, tRNA, rRNA, snRNA, etc.), as well as polypeptides (intracellular, extracellular or surface expressed proteins).

"Differential expression", "differentially expressed", "differential levels", and the like, as used herein refers to a difference in the level of an expression product corresponding to a marker in HTCs in comparison to other mammalian cells, e.g., normal HSCs in particular. The difference can be expressed as an expression ratio or signal ratio, obtained from the quotient of the level of expression of an expression product in HTCs over the level of expression of the same expression product in HSCs. "Differential expression" generally refers to a difference in expression levels of at least about 2 fold, at least about 3 fold, at least about 5 fold, at least about 7 fold, at least about 10 fold, or at least about 15 fold. In particularly preferred embodiments, the difference in expression levels is at least about 20 fold, at least about 30 fold, at least about 40 fold, or at least about 50 fold. In still more preferred embodiments, the difference in expression levels is at least about 70 fold, at least about 100 fold, at least about 200 fold, or as much as nearly 300 fold, 400 fold or 500 fold.

The term "extracellularly-expressed" refers to the case where expression products are found outside of a cell, whether existing entirely outside of the plasma membrane of a cell (as in the case of secreted, soluble products); or existing partly outside of a cell as in the case of some membrane- (or surface-) expressed products. Membrane-bound proteins may be integral or peripheral, so long as at least a portion of the protein is accessible to antibodies outside the cell. The term membrane-bound includes membrane-expressed products as well as receptor bound products that become associated with surface membranes by virtue of binding to a membrane-bound receptor.

"Subject" or "patient" are used interchangeably and refer to, except where indicated, mammals such as humans and non-human primates, as well as rabbits, rats, mice, goats, pigs, and other mammalian species.

"Haematological proliferative disorder" or "hematopoietic proliferative disorder" refers to a condition characterized by the clonal proliferation of one or more hematopoietic cells of the myeloid and/or lymphoid lineage. "Hematological proliferative disorder of the myeloid lineage" refers to conditions characterized by the clonal proliferation primarily of one or more hematopoietic cells of the myeloid lineage, rather than the lymphoid lineage. It is to be noted that herein the term "of myeloid origin" is used interchangeably with the adjectives "myeloid" or "myelogenous." Myelogenous hematopoietic proliferative disorders include, e.g., the general classes of (a) dysmyelopoietic disease, (b) acute myeloproliferative leukemia and (c) chronic myeloproliferative disease. Each general class is further categorized into different subtypes, as is known in the art.

5.2 Hybridomas and Monoclonal Antibodies

The teachings of the present disclosure provide hybridoma cell lines and monoclonal antibodies that specifically bind to one or more of the following cytokine receptor products: colony stimulating factor 1 receptor (CSF1R); interleukin 13 receptor, alpha 1 (IL13RA1); interleukin 1 receptor accessory protein (IL1RAP); interferon-a receptor 1 (IFNAR1); interleukin-5 receptor alpha (IL5RA); insulin receptor (INSR); interleukin 1 receptor-like 1 (IL1RL1); leukocyte receptor tyrosine (LTK); and tumor associated calcium signal transducer 1 (TACSTD1) associated with hematopoietic tumor cells (HTCs) of myeloid origin.

The following cytokine receptor markers are over-expressed on the surface of HTCs of myeloid origin: colony stimulating factor 1 receptor (CSF1R); interleukin 13 receptor, alpha 1 (IL13RA1); interleukin 1 receptor accessory protein (IL1RAP); interferon-a receptor 1 (IFNAR1); interleukin-5 receptor alpha (IL5RA); insulin receptor (INSR); interleukin 1 receptor-like 1 (IL1RL1); leukocyte receptor tyrosine (LTK); and tumor associated calcium signal transducer 1 (TACSTD1). The invention provides anti-CSF1R antibodies; anti-IL13RA1 antibodies; anti-IL1RAP antibodies; anti-IFNAR1 antibodies; anti-IL5RA antibodies; anti-INSR antibodies; anti-IL1RL1 antibodies; anti-LTK antibodies; and anti-TACSTD1 antibodies, where the antibodies are preferably monoclonal antibodies.

CSF1R is a disulfide-linked homodimer, also referred to in the art as CD115, 1436, CSF1R, 164770, P07333, C-FMS, CSFR, FIM2 and FMS, and formerly referred to as McDonough feline sarcoma viral (v-fms) oncogene homolog. CSF1R is normally expressed on myeloid cells, in particular progenitors and monocytes, and osteoclasts as a membrane bound polypeptide. Upon binding to its ligand CSF-1, the receptor undergoes tyrosine autophosphorylation and subsequently, phosphorylates other membrane-proximal downstream targets, resulting in a number of physiological effects, including cytoskeletal remodeling, gene transcription and protein translation. CSF1R activation is known to promote the survival, proliferation and differentiation of mononuclear phagocytes, as well as the spreading and motility of macrophages. In osteoclasts, CSF1R synergizes with RANKL to regulate the differentiation of mononuclear phagocytes to osteoclasts.

The present invention provides anti-CSF1 R antibodies, preferably monoclonal antibodies, that can specifically bind to CSF1R antigen, e.g., CSF1R polypeptide exposed on the surface of HTCs of myeloid origin. As discussed in more detail below, the anti-CSF1 R antibodies preferably bind such myelogenous HTCs, thereby inhibiting their proliferation and/or mediating their destruction. One of skill in the art will further recognize that antibodies known in the art can find use in the methods disclosed in the instant invention. For example, one or more anti-CSF1R antibodies commercially available from ABCAM®, ABGENT®, ABNOVA®, ANTI-GENIX AMAERICA®, EBIOSCIENCE®, GENETEX®, LAB VISION®, LIFESPAN BIOSCIENCES®, MILLIPORE®, NOVUS® BIOLOGICALS, R&D SYSTEMS®, SIGMA-ALDRICH® AND THERMO SCIENTIFIC PIERCE® may also find use with respect to diagnostic and/or therapeutic applications taught herein.

IL13RA1 occurs as 4 different splice variants and is normally found on T and B cells, as well as on endothelial cells. It is also referred to as CD213a1, CD213A1, NR4, IL13RA, IL-13R, IL-13RA and IL-13R-alpha-1. The IL13RA1 polypeptide is a type I transmembrane protein, which interacts with IL4R to form IL13 receptor. The IL13 receptor in turn binds IL13, and can partially replace the common gamma chain in an IL-2 receptor complex.

The present invention provides anti-IL13RA antibodies, preferably monoclonal antibodies, that can specifically bind to IL13RA antigen, e.g., IL13RA polypeptide exposed on the surface of HTCs of myeloid origin. As discussed in more detail below, the anti-IL13RA antibodies preferably bind such myelogenous HTCs, thereby inhibiting their proliferation and/or mediating their destruction. One of skill in the art will further recognize that antibodies known in the art can find use in the methods disclosed in the instant invention. For example, one or more anti-IL13RA antibodies commercially available from ABCAM®, ABNOVA®, ABR-AFFINITY BIOREAGENTS®, ATLAS ANTIBODIES®, CELL SCIENCES®, DIACLONE®, GENETEX®, LIFESPAN BIOSCIENCES®, NOVUS® BIOLOGICALS, R&D SYSTEMS®, and STRATEGIC DAIGNOSTICS® may also find use with respect to diagnostic and/or therapeutic applications taught herein.

IL1RAP, also known as IL1R3, IL-1 RAcP, F1137788, occurs as 11 alternative splice forms, and is normally expressed on macrophages/monocytes, B cells, platelets, thymocytes, T cells and dendritic cells. IL1 RAP is a type I transmembrane protein, but also occurs as a secreted version. The protein is known to generally mediate IL-1 dependent activation of NF-kB.

The present invention provides anti-IL1RAP antibodies, preferably monoclonal antibodies, that can specifically bind to IL1 RAP antigen, e.g., IL1 RAP polypeptide exposed on the surface of HTCs of myeloid origin. As discussed in more detail below, the anti-IL1 RAP antibodies preferably bind such myelogenous HTCs, thereby inhibiting their proliferation and/or mediating their destruction. One of skill in the art will further recognize that antibodies known in the art can find use in the methods disclosed in the instant invention. For example, one or more anti-IL1 RAP antibodies commercially available from ABCAM®, ABNOVA® CORPORATION, GENETEX®, LIFESPAN BIOSCIENCES®, AND NOVUS® BIOLOGICALS may also find use with respect to diagnostic and/or therapeutic applications taught herein.

IFNAR1 is a type I membrane protein that forms one of the two chains of a receptor for interferons alpha and beta. Binding and activation of the receptor stimulates Janus protein kinases, which in turn phosphorylate several proteins, including STAT1 and STAT2. It may also function as an antiviral factor. IFNAR1 is also known as AVP, IFRC, IFNBR, IFN-alpha-REC, IFNAR.

The present invention provides anti-IFNAR1 antibodies, preferably monoclonal antibodies, that can specifically bind to IFNAR1 antigen, e.g., IFNAR1 polypeptide exposed on the surface of HTCs of myeloid origin. As discussed in more detail below, the anti-IFNAR1 antibodies preferably bind such myelogenous HTCs, thereby inhibiting their proliferation and/or mediating their destruction. One of skill in the art will further recognize that antibodies known in the art can find use in the methods disclosed in the instant invention. For example, one or more anti-IFNAR1 antibodies commercially available from ABCAM®, NOVUS® BIOLOGICALS, and R&D SYSTEMS® may also find use with respect to diagnostic and/or therapeutic applications taught herein.

IL5RA is an interleukin 5 specific subunit of a heterodimeric cytokine receptor. The IL5 heterodimeric receptor comprises a ligand specific alpha subunit and a signal transducing beta subunit shared by the receptors for interleukin 3 (IL3) and colony stimulating factor 2 (CSF2/GMCSF). The beta subunit is activated by ligand binding, and is required for biological activity of IL5. IL5RA may interact with the syndecan binding protein (syntenin), which is required for IL5 mediated activation of the transcription factor SOX4. Six alternatively spliced variants encoding three distinct isoforms have been reported. IL5RA is also known as CD125, CDw125, HSIL5R3, and MGC26560.

The present invention provides anti-IL5RA antibodies, preferably monoclonal antibodies, that can specifically bind to IL5RA antigen, e.g., IL5RA polypeptide exposed on the surface of HTCs of myeloid origin. As discussed in more detail below, the anti-IL5RA antibodies preferably bind such myelogenous HTCs, thereby inhibiting their proliferation and/or mediating their destruction. One of skill in the art will further recognize that antibodies known in the art can find use in the methods disclosed in the instant invention. For example, one or more anti-IL5RA antibodies commercially available from ABCAM®, THERMO SCIENTIFIC PIERCE®, GENETEX®, PROTEINTECH®, and ATLAS ANTIBODIES® may also find use with respect to diagnostic and/or therapeutic applications taught herein.

INSR, also known as HHF5 and CD220, stimulates glucose uptake.

The present invention provides anti-INSR antibodies, preferably monoclonal antibodies, that can specifically bind to INSR antigen, e.g., INSR polypeptide exposed on the surface of HTCs of myeloid origin. As discussed in more detail below, the anti-INSR antibodies preferably bind such myelogenous HTCs, thereby inhibiting their proliferation and/or mediating their destruction. One of skill in the art will further recognize that antibodies known in the art can find use in the methods disclosed in the instant invention. For example, one or more anti-INSR antibodies commercially available from R&D DIAGNOSTICS® and LIFESPAN BIOSCIENCES® may also find use with respect to diagnostic and/or therapeutic applications taught herein.

IL1RL1, also known as T1, ST2, DER4, ST2L, ST2V, FIT-1, and MGC32623, is a member of the interleukin 1 receptor family. It may be induced by proinflammatory stimuli, and may be involved in the function of helper T cells.

The present invention provides anti-IL1RL1 antibodies, preferably monoclonal antibodies, that can specifically bind to IL1RL1 antigen, e.g., IL1RL1 polypeptide exposed on the surface of HTCs of myeloid origin. As discussed in more detail below, the anti-IL5RA antibodies preferably bind such myelogenous HTCs, thereby inhibiting their proliferation and/or mediating their destruction. One of skill in the art will further recognize that antibodies known in the art can find use in the methods disclosed in the instant invention. For example, one or more anti-IL1 R1 antibodies commercially available from PROTEIN TECH® may also find use with respect to diagnostic and/or therapeutic applications taught herein.

LTK is a member of the ros/insulin receptor family of tyrosine kinases. Multiple transcript variants encoding different isoforms have been found for this gene. LTK is also known as TYK1.

The present invention provides anti-LTK antibodies, preferably monoclonal antibodies, that can specifically bind to LTK antigen, e.g., LTK polypeptide exposed on the surface of HTCs of myeloid origin. As discussed in more detail below, the anti-LTK antibodies preferably bind such myelogenous HTCs, thereby inhibiting their proliferation and/or mediating their destruction. One of skill in the art will further recognize that antibodies known in the art can find use in the methods disclosed in the instant invention. For example, one or more anti-LTK antibodies commercially available from ABCAM®, ABGENT®, ABNOVA®, LIFESPAN BIOSCIENCES®, NOVUS® BIOLOGICALS, and SANTA CRUZ BIOLOGICALS® may also find use with respect to diagnostic and/or therapeutic applications taught herein.

TACSTD1 is expressed on most normal epithelial cells and gastrointestinal carcinomas. It may function as a homotypic calcium-independent cell adhesion molecule and is used as a target for immunotherapy of human carcinomas. TACSTD1 is also known as EGP, ESA, KSA, M4S1, MK1, EGP2, EGP34, EGP40, KS1/4, MIC18, TROP1, CO-17A, EpCAM, hEGP2, CO17-1A, GA733-2, and TACST-1.

The present invention provides anti-TACSTD1 antibodies, preferably monoclonal antibodies, that can specifically bind to TACSTD1 antigen, e.g., TACSTD1 polypeptide exposed on the surface of HTCs of myeloid origin. As discussed in more detail below, the anti-TACSTD1 antibodies preferably bind such myelogenous HTCs, thereby inhibiting their proliferation and/or mediating their destruction. One of skill in the art will further recognize that antibodies known in the art can find use in the methods disclosed in the instant invention. For example, one or more anti-TACSTD1 antibodies commercially available from LIFESPAN BIOSCIENCES® may also find use with respect to diagnostic and/or therapeutic applications taught herein.

Monoclonal antibodies of the instant disclosure specifically bind myelogenous HTCs by virtue of specific binding to its target antigen. In preferred embodiments, the monoclonal antibody (or a derivative thereof) is specifically immunoreactive with cells of myeloid origin the hematopoietic system, such as granulocyte/macrophage progenitors (GMP), KG-1a, K-562, Jurkat, CML blasts, and AML blasts. For example, in some such embodiments, specific binding to HTCs, by virtue of a cytokine receptor disclosed herein, mediates destruction of hematopoietic tumor cells of myeloid origin.

Antibodies can be produced readily by one skilled in the art. The general methodology for making monoclonal antibodies by hybridomas is now well known to the art. See, e.g., M. Schreier et al., Hybridoma Techniques (Cold Spring Harbor Laboratory); Hammerling et al., Monoclonal Antibodies and T-Cell Hybridomas (Elsevier Biomedical Press). As described above, the present disclosure provides methods of producing the monoclonal antibodies or derivatives thereof. In some embodiments, these methods comprise cultivating a hybridoma cell under suitable conditions, wherein the antibody is produced and obtaining the antibody and/or derivative thereof from the cell and/or from the cell culture medium. A specific example of making the monoclonal antibodies of the instant invention is also provided in the Examples below.

The antibodies can be purified by methods known to the skilled artisan. Purification methods include, among others, selective precipitation, liquid chromatography, HPLC, electrophoresis, chromatofocusing, and various affinity techniques. Selective precipitation may use ammonium sulfate, ethanol (Cohn precipitation), polyethylene glycol, or others available in the art. Liquid chromatography mediums, include, among others, ion exchange medium DEAE, polyaspartate), hydroxylapatite, size exclusion (e.g., those based on crosslinked agarose, acrylamide, dextran, etc.), hydrophobic matrixes (e.g., Blue Sepharose). Affinity techniques typically rely on proteins that interact with the immunoglobulin Fc domain. Protein A from *Staphylococcus aureas* can be used to purify antibodies that are based on human γ1, γ2, or γ4 heavy chains (Lindmark et al., J. Immunol. Meth. 62:1-13 (1983)). Protein G from C and G streptococci is useful for all mouse isotypes and for human .γ3 (Guss et al., EMBO J. 5:15671575 (1986)). Protein L, a *Peptostreptococcus magnus* cell-wall protein that binds immunoglobulins (Ig) through k light-chain interactions (BD Bioscience/ClonTech. Palo Alto, Calif.), is useful for affinity purification of Ig subclasses IgM, IgA, IgD, IgG, IgE and IgY. Recombinant forms of these proteins are also commercially available. If the antibody contains metal binding residues, such as phage display antibodies constructed to contain histidine tags, metal affinity chromatography may be used. When sufficient amounts of specific cell populations are available, antigen affinity matrices may be made with the cells to provide an affinity method for purifying the antibodies.

The present invention provides the antibodies described herein, as well as corresponding antibody fragments and antigen-binding portions. The terms "antibody fragment" or "antigen-binding portion" of an antibody (or simply "antibody portion") of the present invention, as used herein, refers to one or more fragments of an antibody that retain the ability to specifically bind to an antigen. It has been shown that the antigen-binding function of an antibody can be performed by fragments of a full-length antibody. Examples of binding fragments encompassed within the term "antibody fragment" or "antigen-binding portion" of an antibody include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., (1989) Nature 341:544-546), which consists of a $V_H$ domain; and (vi) an isolated complementarity determining region (CDR), and (vii) bispecific single chain Fv dimers (PCT/US92/09965). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies. The antibody fragments may be modified. For example, the molecules may be stabilized by the incorporation of disulphide bridges linking the VH and VL domains (Reiter et al., 1996, *Nature Biotech.* 14:1239-1245).

The present disclosure further provides fragments of the antibodies disclosed herein. Immunoglobulin molecules can be cleaved into fragments. The antigen binding region of the molecule can be divided into either F(ab')$_2$ or Fab fragments. The F(ab')$_2$ fragment is divalent and is useful when the Fc region is either undesirable or not a required feature. The Fab fragment is univalent and is useful when an antibody has a very high avidity for its antigen. Eliminating the Fc region from the antibody decreases non-specific binding between the Fc region and Fc receptor bearing cells. To generate Fab or F(ab)$_2$ fragments, the antibodies are digested with an enzyme. Proteases that cleave at the hinge region of an immunoglobulin molecule preserve the disulfide bond(s) linking the F(ab) domain such that they remain together following cleavage. A suitable protease for this purpose is pepsin. For producing F(ab) fragments, proteases are chosen such that cleavage occurs above the hinge region containing the disulfide bonds that join the heavy chains but which leaves intact the disulfide bond linking the heavy and light chain. A suitable protease for making F(ab) fragments is papain. The fragments are purified by the methods described above, with the exception of affinity techniques requiring the intact Fc region (e.g., Protein A affinity chromatography).

Antibody fragments can be produced by limited proteolysis of antibodies and are called proteolytic antibody fragments. These include, but are not limited to, the following: F(ab')$_2$ fragments, Fab' fragments, Fab'-SH fragments, and Fab fragments. "F(ab')$_2$ fragments" are released from an antibody by limited exposure of the antibody to a proteolytic enzyme, e.g., pepsin or ficin. A F(ab')$_2$ fragment comprises two "arms," each of which comprises a variable region that is directed to and specifically binds a common antigen. The two Fab' molecules are joined by interchain disulfide bonds in the hinge regions of the heavy chains; the Fab' molecules may be directed toward the same (bivalent) or different (bispecific) epitopes. "Fab' fragments" contain a single anti-binding domain comprising a Fab and an additional portion of the heavy chain through the hinge region. "Fab'-SH fragments" are typically produced from F(ab')$_2$ fragments, which are held together by disulfide bond(s) between the H chains in an F(ab')$_2$ fragment. Treatment with a mild reducing agent such as, by way of non-limiting example, beta-mercaptoethylamine, breaks the disulfide bond(s), and two Fab' fragments are released from one F(ab')$_2$ fragment. Fab'-SH fragments are monovalent and monospecific. "Fab fragments" (i.e., an antibody fragment that contains the antigen-binding domain and comprises a light chain and part of a heavy chain bridged by a disulfide bond) are produced by papain digestion of intact antibodies. A convenient method is to use papain immobilized on a resin so that the enzyme can be easily removed and the digestion terminated. Fab fragments do not have the disulfide bond(s) between the H chains present in a F(ab')$_2$ fragment.

"Single-chain antibodies" are one type of antibody fragment. The term single chain antibody is often abbreviated as "scFv" or "sFv." These antibody fragments are produced using molecular genetics and recombinant DNA technology. A single-chain antibody consists of a polypeptide chain that comprises both a $V_H$ and a $V_L$ domains which interact to form an antigen-binding site. The $V_H$ and $V_L$ domains are usually linked by a peptide of 10 to 25 amino acid residues.

The term "single-chain antibody" further includes but is not limited to a disulfide-linked Fv (dsFv) in which two single-chain antibodies (each of which may be directed to a different epitope) linked together by a disulfide bond; a bispecific sFv in which two discrete scFvs of different specificity is connected with a peptide linker; a diabody (a dimerized sFv formed when the $V_H$ domain of a first sFv assembles with the $V_L$ domain of a second sFv and the $V_L$ domain of the first sFv assembles with the $V_H$ domain of the second sFv; the two antigen-binding regions of the diabody may be directed towards the same or different epitopes); and a triabody (a trimerized sFv, formed in a manner similar to a diabody, but in which three antigen-binding domains are created in a single complex; the three antigen binding domains may be directed towards the same or different epitopes).

"Complementary determining region peptides" or "CDR peptides" are another form of an antibody fragment. A CDR peptide (also known as "minimal recognition unit") is a peptide corresponding to a single complementarity-determining region (CDR), and can be prepared by constructing genes encoding the CDR of an antibody of interest. Such genes are prepared, for example, by using the polymerase chain reaction to synthesize the variable region from RNA of antibody-producing cells. See, for example, Larrick et al., Methods: A Companion to Methods in Enzymology 2:106, 1991.

In "cysteine-modified antibodies," a cysteine amino acid is inserted or substituted on the surface of antibody by genetic manipulation and used to conjugate the antibody to another molecule via, e.g., a disulfide bridge. Cysteine substitutions or insertions for antibodies have been described (see U.S. Pat. No. 5,219,996). Methods for introducing Cys residues into the constant region of the IgG antibodies for use in site-specific conjugation of antibodies are described by Stimmel et al. (J. Biol. Chem. 275:330445-30450, 2000).

The present disclosure further provides humanized and non-humanized antibodies. Humanized forms of non-human (e.g., mouse) antibodies are chimeric antibodies that contain minimal sequence derived from non-human immunoglobulin. Generally, humanized antibodies are non-human antibodies that have had the variable-domain framework regions swapped for sequences found in human antibodies. The humanized antibodies may be human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin.

Generally, in a humanized antibody, the entire antibody, except the CDRs, is encoded by a polynucleotide of human origin or is identical to such an antibody except within its CDRs. The CDRs, some or all of which are encoded by nucleic acids originating in a non-human organism, are grafted into the beta-sheet framework of a human antibody variable region to create an antibody, the specificity of which is determined by the engrafted CDRs. The creation of such antibodies is described in, e.g., WO 92/11018, Jones, 1986, *Nature* 321:522-525, Verhoeyen et al., 1988, *Science* 239: 1534-1536. Humanized antibodies can also be generated using mice with a genetically engineered immune system. Roque et al., 2004, *Biotechnol. Prog.* 20:639-654.

The present disclosure further provides humanized and non-humanized antibodies. Humanized forms of non-human (e.g., mouse) antibodies are chimeric antibodies that contain minimal sequence derived from non-human immunoglobulin. Generally, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin.

It can be desirable to modify the antibodies of the invention with respect to effector function, so as to enhance, e.g., the effectiveness of the antibody in treating cancer. For example, cysteine residue(s) can be introduced into the Fc region, thereby allowing interchain disulfide bond formation in this region. The homodimeric antibody thus generated can have improved internalization capability and/or increased complement-mediated cell killing and antibody-dependent cellular cytotoxicity (ADCC). See Caron et al., J. Exp Med., 176: 1191-1195 (1992) and Shopes, J. Immunol., 148:2918-2922 (1992). Homodimeric antibodies with enhanced anti-tumor activity can also be prepared using heterobifunctional cross-linkers as described in Wolff et al. Cancer Research, 53:2560-2565 (1993). Alternatively, an antibody can be engineered that has dual Fc regions and can thereby have enhanced complement lysis and ADCC capabilities. See Stevenson et al., Anti-Cancer Drug Design, 3:219-230 (1989).

In preferred embodiments, the antibodies described herein specifically bind to an antigen corresponding to one or more of the disclosed cytokine receptors present on the cell surface of hematopoietic tumor cells (HTCs) that arose from progenitor cell populations in the myeloid lineage of the hematopoietic system. Differentiation in the myeloid lineage leads to formation of terminally differentiated cells that include, among others, megakaryocytes, erythroid cells, macrophages, basophils, eosinophils, neutrophils and myeloid dendritic cells. These cells originate from hematopoietic stem cells (HSC), which differentiate through a series of progenitor cell populations displaying progressively restricted differentiation potential. The HSCs and the progenitor cell populations are identifiable from each other based on, among other distinguishing characteristics, their capacity to differentiate into specific cell subsets and the presence of a particular set of cellular markers that is specific to the cell population. In some embodiments, the monoclonal antibodies of the present disclosure are directed to progenitor cells of the myeloid lineage that are marker+ HTCs. In some embodiments, the monoclonal antibodies in the present disclosure are directed to committed myeloid progenitor cells that are marker+ HTCs.

5.2.1 Modified Antibodies

In another aspect, the present invention provides modified antibodies that are derived from an antibody that specifically binds an antigen corresponding to a cytokine receptor disclosed herein. Modified antibodies also include recombinant antibodies as described herein.

Numerous types of modified or recombinant antibodies will be appreciated by those of skill in the art. Suitable types of modified or recombinant antibodies include without limitation, engineered murine monoclonal antibodies (e.g. murine monoclonal antibodies, chimeric monoclonal antibodies, humanized monoclonal antibodies), domain antibodies (e.g. Fab, Fv, $V_H$, scFV, and dsFv fragments), multivalent or multispecific antibodies (e.g. diabodies, minibodies, miniantibodies, $(scFV)_2$, tribodies, and tetrabodies), and antibody conjugates as described herein.

In one aspect, the present invention includes domain antibodies. "Domain antibodies" are functional binding domains of antibodies, corresponding to the variable regions of either the heavy (VH) or light (VL) chains of human antibodies. Domain antibodies may have a molecular weight of approximately 13 kDa, or less than one-tenth the size of a full antibody. They are well expressed in a variety of hosts including bacterial, yeast, and mammalian cell systems. In addition, domain antibodies are highly stable and retain activity even after being subjected to harsh conditions, such as freeze-drying or heat denaturation. See, for example, U.S. Pat. Nos. 6,291,158; 6,582,915; 6,593,081; 6,172,197; US Serial No. 2004/0110941; European Patent 0368684; U.S. Pat. No. 6,696,245, WO04/058821, WO04/003019 and WO03/002609. In one embodiment, the domain antibody of the present invention is a single domain. Single domain antibodies may be prepared, for example, as described in U.S. Pat. No. 6,248,516, incorporated herein by reference in its entirety. In some embodiments, the present invention provides domain antibodies derived from an antibody that specifically binds to an antigen corresponding to one of the cytokine receptors disclosed herein.

In another aspect, the present invention includes multi-specific antibodies. Multi-specific antibodies include bispecific, trispecific, etc. antibodies. Bispecific antibodies can be produced via recombinant means, for example by using leucine zipper moieties (i.e., from the Fos and Jun proteins, which preferentially form heterodimers; Kostelny et al., 1992, J. Immunol. 148:1547) or other lock and key interactive domain structures as described in U.S. Pat. No. 5,582,996. Additional useful techniques include those described in U.S. Pat. No. 5,959,083; and U.S. Pat. No. 5,807,706. In one embodiment, the present invention provides multi-specific antibodies that include an antibody that specifically binds an antigen corresponding to a cytokine receptor disclosed herein. In another embodiment, the multispecific antibody is bispecific.

Bispecific antibodies are also sometimes referred to as "diabodies." These are antibodies that bind to two (or more) different antigens. Also known in the art are triabodies (a trimerized sFv, formed in a manner similar to a diabody, but in which three antigen-binding domains are created in a single complex; the three antigen binding domains may be directed towards the same or different epitopes) or a tetrabodies (four antigen-binding domains created in a single complex where the four antigen binding domains may be directed towards the same or different epitopes), and the like. Dia-, tria- and tetrabodies can be manufactured in a variety of ways known in the art (Holliger and Winter, 1993, *Current Opinion Biotechnol.* 4:446-449), e.g., prepared chemically or from hybrid hybridomas. In addition, such antibodies and fragments thereof may be constructed by gene fusion (Tomlinson et. al., 2000, *Methods Enzymol.* 326:461-479; WO94/13804; Holliger et al., 1993, *Proc. Natl. Acad. Sci. U.S.A.* 90:6444-6448, each of which is incorporated herein by reference in their entirety). In one embodiment, the diabody, triabody, or tetrabody is derived from an antibody that specifically binds an antigen corresponding to a cytokine receptor disclosed herein. In a preferred embodiment, the diabody, triabody, or tetrabody is derived from two or more monoclonal antibodies that specifically bind to different antigens, each antigen corresponding to different cytokine receptors disclosed herein.

In another embodiment, the present invention provides minibodies, which are minimized antibody-like proteins that include a scFV joined to a CH3 domain, that are derived from an antibody that specifically binds an antigen corresponding to a cytokine receptor disclosed herein. Minibodies can be made as described in the art (Hu et al., 1996, *Cancer Res.* 56:3055-3061).

In another embodiment, the present invention provides binding domain-immunglobulin fusion proteins, where the binding domain specifically binds an antigen corresponding to a HTC marker disclosed herein. The fusion protein may include a marker specific binding domain polypeptide fused to an immunoglobulin hinge region polypeptide, which is fused to an immunoglobulin heavy chain CH2 constant region polypeptide fused to an immunoglobulin heavy chain CH3 constant region polypeptide. Under the present invention, marker specific antibody fusion proteins can be made by methods appreciated by those of skill in the art (See published U.S. Patent Application Nos. 20050238646, 20050202534, 20050202028, 2005020023, 2005020212, 200501866216, 20050180970, and 20050175614, each of which is incorporated herein by reference in their entirety).

In another embodiment, the present invention provides a heavy-chain protein ($V_{HH}$) derived from a marker specific antibody. Naturally-occurring heavy chain antibodies (e.g. camelidae antibodies having no light chains) have been unitized to develop antibody-derived therapeutic proteins that typically retain the structure and functional properties of naturally-occurring heavy-chain antibodies. They are known in the art as Nanobodies®. Under the present invention, heavy chain proteins ($V_{HH}$) derived from a marker specific heavy chain antibody may be made by methods appreciated by those of skill in the art (See published U.S. Patent Application Nos. 20060246477, 20060211088, 20060149041, 20060115470, and 20050214857, each of which is incorporated herein by reference in their entirety).

In one aspect, the present invention provides a modified antibody that is a human antibody. In one embodiment, the marker specific antibodies described herein are fully human antibodies. "Fully human antibody" or "complete human antibody" refers to a human antibody having only the gene sequence of an antibody derived from a human chromosome. The anti-human marker specific complete human antibody can be obtained by a method using a human antibody-producing mouse having a human chromosome fragment containing the genes for a heavy chain and light chain of a human antibody [see Tomizuka, K. et al., Nature Genetics, 16, p. 133-143, 1997; Kuroiwa, Y. et al., Nuc. Acids Res., 26, p. 3447-3448, 1998; Yoshida, H. et al., Animal Cell Technology: Basic and Applied Aspects vol. 10, p. 69-73 (Kitagawa, Y., Matuda, T. and Iijima, S. eds.), Kluwer Academic Publishers, 1999; Tomizuka, K. et al., Proc. Natl. Acad. Sci. USA, 97, 722-727, 2000] or obtained by a method for obtaining a human antibody derived from a phage display selected from a human antibody library (see Wormstone, I. M. et al., Investigative Ophthalmology & Visual Science. 43(7), p. 2301-8, 2002; Carmen, S. et al., Briefings in Functional Genomics and Proteomics, 1 (2), p. 189-203, 2002; Siriwardena, D. et al., Ophthalmology, 109(3), p. 427-431, 2002).

In one aspect, the present invention provides a marker specific antibody that is an antibody analog, sometimes referred to as "synthetic antibodies." For example, a variety of recent work utilizes either alternative protein scaffolds or artificial scaffolds with grafted CDRs. Such scaffolds include, but are not limited to, mutations introduced to stabilize the three-dimensional structure of the binding protein as well as wholly synthetic scaffolds consisting for example of biocompatible polymers. See, for example, Korndorfer et al., 2003, *Proteins: Structure, Function, and Bioinformatics*, Volume 53, Issue 1:121-129. Roque et al., 2004, *Biotechnol. Prog.* 20:639-654. In addition, peptide antibody mimetics ("PAMs") can be used, as well as work based on antibody mimetics utilizing fibronectin components as a scaffold.

5.2.2 Cross-Linked Antibodies

In one aspect, the present invention provides cross-linked antibodies that include two or more antibodies described herein attached to each other to form antibody complexes. Cross-linked antibodies are also referred to as antibody multimers, homoconjugates, and heteroconjugates. It has been observed in the art that the multimerization of an antibody previously observed to have no signalling activity can result in a multimerized antibody with potent signalling activity. This has been particularly noted in the field of anti-tumor agents. For example, it has been reported that the IgG-IgG homodimerization of anti-CD19, anti-CD20, anti-CD21, anti-CD22, and anti-Her-2 monoclonal antibodies confers potent anti-tumor ability to such homodimers (Ghetie, M. et al. (1997) *Proc. Natl. Acad. Sci., USA*, Vol. 94, pp-7509-7514 incorporated herein by reference in its entirety). In addition, the homodimerization of monoclonal antibodies known to have anti-tumor activity, such as Rituximab®, can lead to an increase in effectiveness as an anti-tumor agent (Ghetie, M. (2001) *Blood*, Vo. 97; 5: 1392-1398 incorporated by reference in its entirety).

In some embodiments, the antibody complexes provided herein include multimeric forms of antibodies directed to one or more of the antigens corresponding to one or more of the cytokine receptors disclosed herein. For example, antibodies complexes of the invention may take the form of antibody dimers, trimers, or higher-order multimers of monomeric immunoglobulin molecules. Crosslinking of antibodies can be done through various methods know in the art. For example, crosslinking of antibodies may be accomplished through natural aggregation of antibodies, through chemical or recombinant linking techniques or other methods known in the art. For example, purified antibody preparations can spontaneously form protein aggregates containing antibody homodimers, and other higher-order antibody multimers. In one embodiment, the present invention provides homodimerized antibodies that specifically bind to an antigen corresponding to a cytokine receptor disclosed herein.

Antibodies can be cross-linked or dimerized through linkage techniques known in the art (see Ghetie et al. (1997) supra; Ghetie et al. (2001) supra). Non-covalent methods of attachment may be utilized. In a specific embodiment, crosslinking of antibodies can be achieved through the use of a secondary crosslinker antibody. The crosslinker antibody can be derived from a different animal compared to the antibody of interest. For example, a goat anti-mouse antibody (Fab specific) may be added to a mouse monoclonal antibody to form a heterodimer. This bivalent crosslinker antibody recognizes the Fab or Fc region of the two antibodies of interest forming a homodimer.

In one embodiment of the present invention, an antibody that specifically binds to an antigen corresponding to a cytokine receptor disclosed herein is cross-linked using a goat anti-mouse antibody (GAM). In another embodiment, the GAM crosslinker recognizes the Fab or Fc region of two antibodies, each of which specifically binds the same or two different antigens corresponding to the same or different cytokine receptors disclosed herein.

Methods for covalent or chemical attachment of antibodies may also be utilized. Chemical crosslinkers can be homo or heterobifunctional and will covalently bind with two antibodies forming a homodimer. Cross-linking agents are well known in the art; for example, homo- or hetero-bifunctional linkers as are well known (see the 2006 Pierce Chemical Company Crosslinking Reagents Technical Handbook; Hermanson, G. T., Bioconjugate Techniques, Academic Press, San Diego, Calif. (1996); Aslam M. and Dent A H., Bioconjugation: protein coupling techniques for the biomedical sciences, Houndsmills, England: Macmillan Publishers (1999); Pierce: Applications Handbook & Catalog, Perbio Science, Ermbodegem, Belgium (2003-2004); Haughland, R. P., Handbook of Fluorescent Probes and Research Chemicals Eugene, 9th Ed., Molecular Probes, OR (2003); and U.S. Pat. No. 5,747,641; all references incorporated herein by reference) Those of skill in the art will appreciate the suitability of various functional groups on the amino acid(s) of an antibody for modification, including cross-linking Suitable examples of chemical crosslinkers used for antibody crosslinking include, but not limited to, SMCC [succinimidyl 4-(maleimidomethyl)cyclohexane-1-carboxylate], SATA [N-succinimidyl S-acetylthio-acetate], hemi-succinate esters of N-hydroxysuccinimide; sulfo-N-hydroxy-succinimide; hydroxybenzotriazole, and p-nitrophenol; dicyclohexylcarbodiimide (DCC), 1-(3-dimethylaminopropyl)-3-ethylcarbodiimide (ECD), and 1-(3-dimethylaminopropyl)-3-ethylcarbodiimide methiodide (EDCI) (see, e.g., U.S. Pat. No. 4,526,714, the disclosure of which is fully incorporated by reference herein). Other linking reagents include glutathione, 3-(diethoxyphosphoryloxy)-1,2,3-benzotriazin-4(3H)-one (DEPBT), onium salt-based coupling reagents, polyoxyethylene-based heterobifunctional cross-linking reagents, and other reagents (Haitao, et al., Organ Lett 1:91-94 (1999); Albericio et al., J Organic Chemistry 63:9678-9683 (1998); Arpicco et al., Bioconjugate Chem. 8:327-337 (1997); Frisch et al., Bioconjugate Chem. 7:180-186 (1996); Deguchi et al., Bioconjugate Chem. 10:32-37 (1998); Beyer et al., J. Med. Chem. 41:2701-2708 (1998); Drouillat et al., J. Pharm. Sci. 87:25-30 (1998); Trimble et al., Bioconjugate Chem. 8:416-423 (1997)).

Exemplary protocols for the formation of antibody homodimers is given in U.S. Patent Publication 20060062786, and Ghetie et al., (1997) supra, which are hereby incorporated by reference in their entirety. In a preferred embodiment, the chemical cross-linker used is an SMCC or SATA crosslinker.

In addition, the antibody-antibody conjugates of this invention can be covalently bound to each other by techniques known in the art such as the use of the heterobifunctional cross-linking reagents, GMBS (maleimidobutryloxy succinimide), and SPDP (N-succinimidyl 3-(2-pyridyldithio)propionate) [see, e.g., Hardy, "Purification And Coupling Of Fluorescent Proteins For Use In Flow Cytometry", Handbook Of Experimental Immunology, Volume 1, Immunochemistry, Weir et al. (eds.), pp. 31.4-31.12 4th Ed., (1986), and Ledbetter et al. U.S. Pat. No. 6,010,902, each of which is incorporated herein by reference in their entirety].

In addition, antibodies may be linked via a thioether cross-link as described in U.S. Patent Publication 20060216284, U.S. Pat. No. 6,368,596, which is incorporated herein by reference. As will be appreciated by those skilled in the art, antibodies can be crosslinked at the Fab region. In some embodiments, it is desirable that the chemical crosslinker not interact with the antigen-binding region of the antibody as this may affect antibody function.

5.2.3 Conjugated Antibodies

The antibodies disclosed herein can be conjugated to inorganic or organic compounds, including, by way of example and not limitation, other proteins, nucleic acids, carbohydrates, steroids, and lipids (see for example Green, et al., Cancer Treatment Reviews, 26:269-286 (2000). The compound may be bioactive. Bioactive refers to a compound having a physiological effect on the cell as compared to a cell not exposed to the compound. A physiological effect is a change in a biological process, including, by way of example and not limitation, DNA replication and repair, recombination, transcription, translation, secretion, membrane turnover, cell adhesion, signal transduction, cell death, and the like. A bioactive compound includes pharmaceutical compounds.

In one aspect, the antibodies are conjugated to or modified to carry a detectable compound. Conjugating antibodies to detectable enzymes, fluorochromes, or ligands provides a signal for visualization or quantitation of the target antigen. Antibodies may be labeled with various enzymes to provide highly specific probes that both visualize the target and amplify the signal by acting on a substrate to produce a colored or chemiluminescent product. Horseradish peroxidase, alkaline phosphatase, glucose oxidase, and β-galactosidase are the commonly used enzymes for this purpose. Fluorochromes, such as fluorescein isothiocyanate, tetramethylrhodamine isothiocyanate (TRITC), phycoerythrin, and Cy5, provide a colored reagent for visualization and detection. Suitable fluorescent compounds are described in Haughland, R. P., Handbook of Fluorescent Probes and Research Chemicals Eugene, 9th Ed., Molecular Probes, OR (2003).

In another aspect, the conjugated compounds are chelating ligands, or macrocyclic organic chelating compounds, particularly metal chelating compounds used to image intracellular ion concentrations or used as contrast agents for medical imaging purposes. Chelating ligands are ligands that can bind with more than one donor atom to the same central metal ion. Chelators or their complexes have found applications as MRI contrast agents, radiopharmaceutical applications, and luminescent probes. Conjugates of chelating compounds useful for assessing intracellular ion concentrations may be voltage sensitive dyes and non-voltage sensitive dyes. Exemplary dye molecules for measuring intracellular ion levels include, by way of example and not limitation, Quin-2; Fluo-3; Fura-Red; Calcium Green; Calcium Orange 550 580; Calcium Crimson; Rhod-2 550 575; SPQ; SPA; MQAE; Fura-2; Mag-Fura-2; Mag-Fura-5; Di-4-ANEPPS; Di-8-ANEPPS; BCECF; SNAFL-1; SBFI; and SBFI.

In another embodiment, the ligands are chelating ligands that bind paramagnetic, superparamagnetic or ferromagnetic metals. These are useful as contrast agents for medical imaging and for delivery of radioactive metals to selected cells. Metal chelating ligands, include, by way of example and not limitation, diethylenetriaminepenta acetic acid (DTPA); diethylenetriaminepenta acetic acid bis(methylamide); macrocyclic tetraamine 1,4,7,10-tetraazacyclododecane-N,$N^1$, $N^\circ$,$N^{\circ 1}$-tetraacetic acid (DOTA); and porphyrins (see, e.g., The Chemistry of Contrast Agents in Medical Magnetic Resonance Imaging, Merbach A. E. and Toth E., Ed., Wiley Interscience (2001)). Paramagnetic metal ions, which are detectable in their chelated form by magnetic resonance imaging, include, for example, iron(III), gadolinium(III), manganese (II and III), chromium(III), copper(II), dysprosium(III), terbium(III), holmium (III), erbium (III), and europium (III). Paramagnetic metal ions particularly useful as magnetic resonance imaging contrast agents comprise iron (III) and gadolinium(III) metal complexes. Other paramagnetic, superparamagnetic or ferromagnetic are well known to those skilled in the art.

In another embodiment, the metal-chelate comprises a radioactive metal. Radioactive metals may be used for diagnosis or as therapy based on delivery of small doses of radiation to a specific site in the body. Targeted metalloradiopharmaceuticals are constructed by attaching the radioactive metal ion to a metal chelating ligand, such as those used for magnetic imaging, and delivering the chelate-complex to cells. An exemplary radioactive metal chelate complex is DTPA (see, e.g., U.S. Pat. No. 6,010,679).

In a further aspect, the conjugated compounds are peptide tags used for purposes of detection, particularly through the use of antibodies directed against the peptide. Various tag polypeptides and their respective antibodies are well known in the art. Examples include poly-histidine (poly-his) or poly-histidine-glycine (poly-his-gly) tags; the flu HA tag polypeptide and its antibody 12CA5 (Field et al., Mol. Cell. Biol. 8:2159-2165 (1988)); the c-myc tag and the 8F9, 3C7, 6E10, G4, B7 and 9E10 antibodies thereto (Evan et al., Mol. Cell. Biol. 5:3610-3616 (1985)); and the Herpes Simplex virus glycoprotein D (gD) tag and its antibody (Paborsky et al., Protein Engineering 3:547-553 (1990)). Other tag polypeptides include the Flag-peptide (Hopp et al., BioTechnology 6:1204-1210 (1988)); the KT3 epitope peptide (Martin et al., Science 255:192-194 (1992)); tubulin epitope peptide (Skinner et al., J. Biol. Chem. 266:15163-15166 (1991)); and the T7 gene 10 protein peptide tag (Lutz-Freyermuth et al., Proc. Natl. Acad. Sci. USA 87:6393-6397 (1990)).

In another embodiment, the conjugated compounds may comprise toxins that cause cell death, or impair cell survival when introduced into a cell. A suitable toxin is *Campylobacter* toxin CDT (Lara-Tejero, M., Science 290:354-57 (2000)). Expression of the CdtB subunit, which has homology to nucleases, causes cell cycle arrest and ultimately cell death. Another exemplary toxin is diptheria toxin (and similar *Pseudomonas* exotoxin), which functions by ADP ribosylating ef-2 (elongation factor 2) molecule in the cell and preventing translation. Entry of the diptheria toxin A subunit induces cell death in cells containing the toxin fragment. Other useful toxins include cholera toxin and pertussis toxin (catalytic subunit-A ADP ribosylates the G protein regulating adenylate cyclase), pierisin from cabbage butterflys, an inducers of apoptosis in mammalian cells (Watanabe, M., Proc. Natl. Acad. Sci. USA 96:10608-13 (1999)), ribosome inactivating toxins (e.g., ricin A chain, Gluck, A. et al., J. Mol. Biol. 226:411-24 (1992)); and nigrin (Munoz, R. et al., Cancer Lett. 167: 163-69 (2001)).

Bioactive compounds suitable for delivery by the compositions herein, include, among others, chemotherapeutic compounds, including by way of example and not limitation, vinblastin, bleomycin, taxol, cis-platin, adriamycin, and mitomycin. Exemplary chemotherapeutic agents suitable for the present purposes are compounds acting on DNA synthesis and stability. For example, anti-neoplastic agents of the anthracyclin class of compounds act by causing strand breaks in the DNA and are used as standard therapy against cancer. Exemplary anti-neoplastic agents of this class are daunorubicin and doxorubicin. Coupling of these compounds to proteins, including antibodies, are described in Langer, M. et al., J. Med. Chem. 44(9):1341-1348 (2001) and King, H. D. et al., Bioconjug. Chem. 10:279-288 (1999)). By attaching or linking the antineoplastic agents to the antibodies, the compounds are delivered to HTCs of myeloid origin with a high degree of specificity and promote killing of the targeted cells.

Other classes of antitumor agents are the enediyne family of antibiotics, representative members of which include calicheamicins, neocarzinostatin, esperamincins, dynemicins, kedarcidin, and maduropeptin (see, e.g., Smith, A. L and Nicolaou, K. C., J. Med. Chem. 39:2103-2117 (1996)). Similar to doxorubicin and daunorubicin, the antitumor activity of these agents resides in their ability to create strand breaks in the cellular DNA. Conjugates to antibodies have been used to deliver these molecules into those tumor cells expressing antigens recognized by the antibody and shown to have potent antitumor activity with reduced unwanted toxicity as compared to the unconjugated compounds (Hinman, L M. et al., Cancer Res. 53:3336-3342 (1993)). Conjugating the enediyne compounds to the compositions described herein provides another method of targeting HTCs of myeloid origin.

Radioactive compounds are useful as signals (e.g., tracers) or used to provide a therapeutic effect by their delivery to a cell targeted (e.g., in the form of radiopharmaceutical preparations) and may be attached to the antibodies by methods described below. Useful radioactive nuclides include, by way of example and not limitation, $^3$H, $^{14}$C, $^{32}$P, $^{35}$S, $^{51}$Cr, $^{57}$Co $^{59}$Fe, $^{67}$Ga, $^{82}$Rb, $^{89}$Sr, $^{99}$Tc, $^{111}$In, $^{123}$I, $^{125}$I, $^{129}$I, $^{131}$I, and $^{186}$Re.

The conjugation of compounds to antibodies is well known to the skilled artisan, and typically takes advantage of functional groups present on or introduced onto the antibodies and compound. Functional groups include, among others, hydroxyl, amino, thio, imino, and carboxy moieties. Reaction between functional groups may be aided by coupling reagents and crosslinking agents. Crosslinking agents and linkers and corresponding methods for conjugation are described in Hermanson, G. T., Bioconjugate Techniques, Academic Press, San Diego, Calif. (1996); Aslam M. and Dent A H., Bioconjugation: protein coupling techniques for the biomedical sciences, Houndsmills, England: Macmillan Publishers (1999); Pierce: Applications Handbook & Catalog, Perbio Science, Ermbodegem, Belgium (2003-2004); Haughland, R. P., Handbook of Fluorescent Probes and Research Chemicals Eugene, 9th Ed., Molecular Probes, OR (2003); and U.S. Pat. No. 5,747,641; all references incorporated herein by reference. Exemplary coupling or linking reagents include, by way of example and not limitation, hemi-succinate esters of N-hydroxysuccinimide; sulfo-N-hydroxy-succinimide; hydroxybenzotriazole, and p-nitrophenol; dicyclohexylcarbodiimide (DCC), 1-(3-dimethylaminopropyl)-3-ethylcarbodiimide (ECD), and 1-(3-dimethylaminopropyl)-3-ethylcarbodiimide methiodide (EDCI) (see, e.g., U.S. Pat. No. 4,526,714) the disclosure of which is fully incorporated by reference herein. Other linking reagents include glutathione, 3-(diethoxyphosphoryloxy)-1,2,3-benzotriazin-4(3H)-one (DEPBT), onium salt-based coupling reagents, polyoxyethylene-based heterobifunctional cross-linking reagents, and other reagents that facilitate the coupling of antibodies to organic drugs and peptides and other ligands (Haitao, et al., Organ Lett 1:91-94 (1999); Albericio et al., J Organic Chemistry 63.9678-9683 (1998); Arpicco et al., Bioconjugate Chem. 8.327-337 (1997); Frisch et al., Bioconjugate Chem. 7:180-186 (1996); Deguchi et al., Bioconjugate Chem. 10:32-37 (1998); Beyer et al., J. Med. Chem. 41:2701-2708 (1998); Drouillat et al., J. Pharm. Sci. 87:25-30 (1998); Trimble et al., Bioconjugate Chem. 8:416-423 (1997)).

Techniques for conjugating therapeutic compounds to antibodies are also described in Amon et al., "Monoclonal Antibodies for Immunotargeting of Drugs in Cancers Therapy," in Monoclonal Antibodies and Cancer Therapy, Reisfeld et al., ed., pp 243-256, Alan R. Liss, Inc. (1985); Thorpe, et al. "The Preparation and Cytotoxic Properties of Antibody Toxin Conjugates," Immunol. Rev. 62:119-58 (1982); and Pietersz, G. A., "The linkage of cytotoxic drugs to monoclonal antibodies for the treatment of cancer," Bioconjugate Chemistry 1(2): 89-95 (1990), all references incorporated herein by reference.

6. Antisense Molecules and Small Molecule Compounds

Another aspect of the present invention relates to antisense and sense molecules comprising a single-stranded nucleic acid sequence (either RNA or DNA) that can bind to mRNA (sense) or DNA (antisense) target sequences corresponding to a cytokine receptor disclosed herein. Antisense or sense oligonucleotides, according to the present invention, comprise a fragment of the coding region of DNA of the gene corresponding to a cytokine receptor. Such a fragment generally comprises at least about 14 nucleotides, preferably from about 14 to about 30 nucleotides. Antisense or sense RNA or DNA molecules are generally at least about 5 nucleotides in length, alternatively at least about 15, at least about 30, at least about 50, at least about 100, at least about 150, at least about 200, at least about 300, at least about 400, at least about 500, at least about 700, at least about 800, or at least about 1000 nucleotides in length. The ability to derive an antisense or a sense oligonucleotide, based upon a cDNA sequence encoding a given protein is described in, for example, Stein and Cohen (Cancer Res. 48:2659, 1988) and van der Krol et al. (BioTechniques 6:958, 1988).

Binding of antisense or sense oligonucleotides to target nucleic acid sequences results in the formation of duplexes that block transcription or translation of the target sequence by one of several means, including enhanced degradation of the duplexes, premature termination of transcription or translation, or by other means. Such methods are encompassed by the present invention. The antisense oligonucleotides thus may be used to block the expression of proteins corresponding to a cytokine receptor, wherein those marker proteins may play a role in the induction and/or persistence of myeloid leukemias in mammals.

Preferred intragenic sites for antisense binding include the region incorporating the translation initiation/start codon (5'-AUG/5'-ATG) or termination/stop codon (5'-UAA, 5'-UAG and 5-UGA/5'-TAA, 5'-TAG and 5'-TGA) of the open reading frame (ORF) of the gene. These regions refer to a portion of the mRNA or gene that encompasses from about 25 to about 50 contiguous nucleotides in either direction (i.e., 5' or 3') from a translation initiation or termination codon. Other preferred regions for antisense binding include: introns; exons; intron-exon junctions; the open reading frame (ORF) or "coding region," which is the region between the translation initiation codon and the translation termination codon; the 5' cap of an mRNA which comprises an N7-methylated guanosine residue joined to the 5'-most residue of the mRNA via a 5'-5" triphosphate linkage and includes 5' cap structure itself as well as the first 50 nucleotides adjacent to the cap; the 5' untranslated region (5'UTR), the portion of an mRNA in the 5' direction from the translation initiation codon, and thus including nucleotides between the 5' cap site and the translation initiation codon of an mRNA or corresponding nucleotides on the gene; and the 3' untranslated region (3'UTR), the portion of an mRNA in the 3' direction from the translation termination codon, and thus including nucleotides between the translation termination codon and 3' end of an mRNA or corresponding nucleotides on the gene.

Antisense or sense oligonucleotides further comprise oligonucleotides having modified sugar-phosphodiester backbones (or other sugar linkages, such as those described in WO 91/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleotide sequences. Oligonucleotides having modified backbones include those that retain a phosphorus atom in the backbone and those that do not have a phosphorus atom in the backbone. In other embodiments, both the sugar and the internucleoside linkage, i.e., the backbone, of the nucleotide units are replaced with different groups. A further modification includes Locked Nucleic Acids (LNAs) in which the 2'-hdroxyl group is linked to the 3' or 4' carbon atom of the sugar ring to form a bycyclic sugar moiety. The sense or antisense oligonucleotide molecules may also include nucleobase (base) modifications or substitutions.

The antisense and sense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare modified oligonucleotides. The compounds of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption.

Antisense or sense oligonucleotides may be introduced into a cell containing the target nucleic acid sequence by any gene transfer method, including, for example, $CaPO_4$-mediated DNA transfection, electroporation, or by using gene transfer vectors such as Epstein-Barr virus. In a preferred procedure, an antisense or sense oligonucleotide is inserted into a suitable retroviral vector. A cell containing the target nucleic acid sequence is contacted with the recombinant retroviral vector, either in vivo or ex vivo. Suitable retroviral vectors include, but are not limited to, those derived from the murine retrovirus M-MuLV, N2 (a retrovirus derived from M-MuLV), or the double copy vectors designated DCT5A, DCT5B and DCT5C (see WO 90/13641).

Sense or antisense oligonucleotides also may be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell. Alternatively, a sense or an antisense oligonucleotide may be introduced into a cell containing the target nucleic acid sequence by formation of an oligonucleotide-lipid complex, as described in WO 90/10448. The sense or antisense oligonucleotide-lipid complex is preferably dissociated within the cell by an endogenous lipase.

In another embodiment, the invention provides small molecules, which bind, preferably specifically, to one or more of the cytokine receptor polypeptides disclosed herein. In preferred embodiments, the small molecule is a small organic molecule, including small organic molecules known in the art as being an agonist or antagonist of a polypeptide corresponding to a cytokine receptor disclosed herein.

In some embodiments, the small molecule is conjugated to a growth inhibitory agent or cytotoxic agent such as a toxin. Such toxins include, for example, a maytansinoid or calicheamicin, an antibiotic, a radioactive isotope, a nucleolytic enzyme, or the like. The small molecules that find use in the therapeutic methods of the instant invention preferably induce death of a cell to which they bind. As detailed above, binding to HTCs of myeloid origin may occur by virtue of binding to a surface-expressed marker disclosed herein; or by virtue of binding to the surface-expressed marker, which itself is bound to its receptor on myelogenous HTCs.

7. Pharmaceutical Compositions

In the preparation of pharmaceutical compositions comprising the antibodies and/or antisense molecules and/or small molecule agonists or antagonists described in the teachings herein, a variety of vehicles and excipients and routes of administration may be used, as will be apparent to the skilled artisan. Representative formulation technology is taught in, inter alia, Remington: The Science and Practice of Pharmacy, 19th Ed., Mack Publishing Co., Easton, Pa. (1995) and Handbook of Pharmaceutical Excipients, 3rd Ed, Kibbe, A. H. ed., Washington D.C., American Pharmaceutical Association (2000); hereby incorporated by reference in their entirety.

The pharmaceutical compositions will generally comprise a pharmaceutically acceptable carrier and a pharmacologically effective amount of the antibodies, or mixture of antibodies, or suitable salts thereof. Use of a mixture of monoclonal antibodies specific to a progenitor cell population as a therapeutic has a number of advantages. Abnormally proliferating cells have a tendency to mutate, and thus may lose the antigen recognized by a single type of monoclonal antibody. Moreover, antigen density of a single target antigen in the targeted cell could be low such that there is insufficient triggering of the signals necessary for destruction of the cell by the immune system. The present disclosure addresses these issues by providing multiple cytokine receptors associated with HTCs of myeloid origin that can be targeted by a mixture of different monoclonal antibodies.

For known small molecule agonists or antagonists, pharmaceutical compositions can similarly be prepared based on known characteristics of the molecules.

The pharmaceutical composition may be formulated as powders, granules, solutions, suspensions, aerosols, solids, pills, tablets, capsules, gels, topical cremes, suppositories, transdermal patches, and other formulations known in the art.

For the purposes described herein, pharmaceutically acceptable salts of the antibodies is intended to include any art recognized pharmaceutically acceptable salts including organic and inorganic acids and/or bases. Examples of salts include sodium, potassium, lithium, ammonium, calcium, as well as primary, secondary, and tertiary amines, esters of lower hydrocarbons, such as methyl, ethyl, and propyl. Other salts include organic acids, such as acetic acid, propionic acid, pyruvic acid, maleic acid, succinic acid, tartaric acid, citric acid, benzoic acid, cinnamic acid, salicylic acid, etc.

As used herein, "pharmaceutically acceptable carrier" comprises any standard pharmaceutically accepted carriers known to those of ordinary skill in the art in formulating pharmaceutical compositions. Thus, the antibodies, by themselves, such as being present as pharmaceutically acceptable salts, or as conjugates, may be prepared as formulations in pharmaceutically acceptable diluents; for example, saline, phosphate buffer saline (PBS), aqueous ethanol, or solutions of glucose, mannitol, dextran, propylene glycol, oils (e.g., vegetable oils, animal oils, synthetic oils, etc.), microcrystalline cellulose, carboxymethyl cellulose, hydroxylpropyl methyl cellulose, magnesium stearate, calcium phosphate, gelatin, polysorbate 80 or the like, or as solid formulations in appropriate excipients.

The pharmaceutical compositions will often further comprise one or more buffers (e.g., neutral buffered saline or phosphate buffered saline), carbohydrates (e.g., glucose, mannose, sucrose or dextrans), mannitol, proteins, polypeptides or amino acids such as glycine, antioxidants (e.g., ascorbic acid, sodium metabisulfite, butylated hydroxytoluene, butylated hydroxyanisole, etc.), bacteriostats, chelating agents such as EDTA or glutathione, adjuvants (e.g., aluminium hydroxide), solutes that render the formulation isotonic, hypotonic or weakly hypertonic with the blood of a recipient, suspending agents, thickening agents and/or preservatives. Alternatively, compositions of the present invention may be formulated as a lyophilizate.

While any suitable carrier known to those of ordinary skill in the art may be employed in the compositions of this invention, the type of carrier will typically vary depending on the mode of administration. Antibody compositions may be formulated for any appropriate manner of administration, including for example, oral, nasal, mucosal, intravenous, intraperitoneal, intradermal, subcutaneous, and intramuscular administration.

For parenteral administration, the compositions can be administered as injectable dosages of a solution or suspension of the substance in a physiologically acceptable diluent with a pharmaceutical carrier that can be a sterile liquid such as sterile pyrogen free water, oils, saline, glycerol, polyethylene glycol or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, non-aqueous solutions of peanut oil, soybean oil, corn oil, cottonseed oil, ethyl oleate, and isopropyl myristate. Antibodies can be administered in the form of a depot injection or implant preparation which can be formulated in such a manner as to permit a sustained release of the active ingredient. An exemplary composition comprises antibody at 5 mg/ml, formulated in aqueous buffer consisting of 50 mM L-histidine, 150 mM NaCl, adjusted to pH 6.0 with HCl.

Typically, the compositions are prepared as injectables, either as liquid solutions or suspensions; solid or powder forms suitable for reconstitution with suitable vehicles, including by way example and not limitation, sterile pyrogen free water, saline, buffered solutions, dextrose solution, etc., prior to injection. The preparation also can be emulsified or encapsulated in liposomes or micro particles such as polylactide, polyglycolide, or copolymers, as further discussed below (see, e.g., Langer, Science 249:1527 (1990) and Hanes, Advanced Drug Delivery Rev. 28:97-119 (1997)).

Additionally, the compositions may also be introduced or encapsulated into the lumen of liposomes for delivery and for extending their life time ex vivo or in vivo. As known in the art, liposomes can be categorized into various types: multilamellar (MLV), stable plurilamellar (SPLV), small unilamellar (SUV) or large unilamellar (LUV) vesicles. Liposomes can be prepared from various lipid compounds, which may be synthetic or naturally occurring, including phosphatidyl ethers and esters, such as phosphotidylserine, phosphotidylcholine, phosphatidyl ethanolamine, phosphatidylinositol, dimyristoylphosphatidylcholine; steroids such as cholesterol; cerebrosides; sphingomyelin; glycerolipids; and other lipids (see, e.g., U.S. Pat. No. 5,833,948).

Cationic lipids are also suitable for forming liposomes. Generally, the cationic lipids have a net positive charge and have a lipophilic portion, such as a sterol or an acyl or diacyl side chain. Preferably, the head group is positively charged. Typical cationic lipids include 1,2-dioleyloxy-3-(trimethylamino)propane; N-[1-(2,3,-ditetradecycloxy)propyl]-N,N-dimethyl-N-hydroxyethylammonium bromide; N-[1-(2,3-dioleyloxy)propyl]-N,N-dimethyl-N-hydroxy ethylammonium bromide; N-[1-(2,3-dioleyloxy) propyl]-N,N,N-trimethylammonium chloride; 3[N—(N',N'-dimethylaminoethane) carbamoyl]cholesterol; and dimethyldioctadecylammonium.

Liposomes also include vesicles derivatized with a hydrophilic polymer, as provided in U.S. Pat. Nos. 5,013,556 and 5,395,619, hereby incorporated by reference, (see also, Kono, K. et al., J. Controlled Release 68: 225-35 (2000); Zalipsky, S. et al., Bioconjug. Chem. 6: 705-708 (1995)) to extend the circulation lifetime in vivo. Hydrophilic polymers for coating or derivation of the liposomes include polyethylene glycol, polyvinylpyrrolidone, polyvinylmethyl ether, polyaspartamide, hydroxymethyl cellulose, hydroxyethyl cellulose, and the like.

Liposomes are prepared by ways well known in the art (see, e.g., Szoka, F. et al., Ann. Rev. Biophys. Bioeng. 9: 467-508 (1980)). One typical method is the lipid film hydration technique in which lipid components are mixed in an organic solvent followed by evaporation of the solvent to generate a lipid film. Hydration of the film in aqueous buffer solution, preferably containing the subject antibodies, results in an emulsion, which is sonicated or extruded to reduce the size and polydispersity. Other methods include reverse-phase evaporation (see, e.g., Pidgeon, C. et al., Biochemistry 26: 17-29 (1987); Duzgunes, N. et al., Biochim. Biophys. Acta. 732: 289-99 (1983)), freezing and thawing of phospholipid mixtures, and ether infusion.

In another embodiment, the carriers are in the form of microparticles, microcapsules, microspheres and nanoparticles, which may be biodegradable or non-biodegradable (see, e.g., "Microencapsulates: Methods and Industrial Applications," in Drugs and Pharmaceutical Sciences, Benita, S. ed, Vol 73, Marcel Dekker Inc., New York (1996); incorporated herein by reference). As used herein, microparticles, microspheres, microcapsules and nanoparticles mean a particle, which is typically a solid, containing the substance to be delivered. The substance is within the core of the particle or attached to the particle's polymer network. Generally, the difference between microparticles (or microcapsules or microspheres) and nanoparticles is one of size. As used herein, microparticles have a particle size range of about 1 to about >1000 microns. Nanoparticles have a particle size range of about 10 to about 1000 nm.

A variety of materials are useful for making microparticles. Non-biodegradable microcapsules and microparticles include, but not limited to, those made of polysulfones, poly (acrylonitrile-co-vinyl chloride), ethylene-vinyl acetate, hydroxyethylmethacrylate-methyl-methacrylate copolymers. These are useful for implantation purposes where the encapsulated composition diffuses out from the capsules. In another aspect, the microcapsules and microparticles are based on biodegradable polymers, preferably those that display low toxicity and are well tolerated by the immune system. These include protein based microcapsulates and microparticles made from fibrin, casein, serum albumin, collagen, gelatin, lecithin, chitosan, alginate or poly-amino acids such as poly-lysine. Biodegradable synthetic polymers for encapsulating may comprise polymers such as polylactide (PLA), polyglycolide (PGA), poly(lactide-co-glycolide) (PLGA), poly(caprolactone), polydioxanone trimethylene carbonate, polyhybroxyalkonates (e.g., poly($\beta$-hydroxybutyrate)), poly ($\gamma$-ethyl glutamate), poly(DTH iminocarbony (bisphenol A iminocarbonate), poly (ortho ester), and polycyanoacrylate. Various methods for making microparticles containing the subject compositions are well known in the art, including solvent removal process (see, e.g., U.S. Pat. No. 4,389,330); emulsification and evaporation (Maysinger, D. et al., Exp. Neuro. 141: 47-56 (1996); Jeffrey, H. et al., Pharm. Res. 10: 362-68 (1993)), spray drying, and extrusion methods.

Another type of carrier is nanoparticles, which are generally suitable for intravenous administrations. Submicron and nanoparticles are generally made from amphiphilic diblock, triblock, or multiblock copolymers as is known in the art. Polymers useful in forming nanoparticles include, but are limited to, poly(lactic acid) (PLA; see Zambaux et al., J. Control Release 60:179-188 (1999)), poly(lactide-co-glycolide), blends of poly(lactide-co-glycolide) and polycarprolactone, diblock polymer poly(l-leucine-block-1-glutamate), diblock and triblock poly(lactic acid) (PLA) and polyethylene oxide) (PEO) (De Jaeghere, F. et al., Pharm. Dev. Technol.; 5: 473-83 (2000)), acrylates, arylamides, polystyrene, and the like. As described for microparticles, nanoparticles may be non-biodegradable or biodegradable. Nanoparticles may be also be made from poly(alkylcyanoacrylate), for example poly(butylcyanoacrylate), in which the therapeutic composition is absorbed onto the nanoparticles and coated with surfactants (e.g., polysorbate 80). Methods for making nanoparticles are similar to those for making microparticles and include, among others, emulsion polymerization in continuous aqueous phase, emulsification-evaporation, solvent displacement, and emulsification-diffusion techniques (see, e.g., Kreuter, J. Nano-particle Preparation and Applications, in Microcapsules and Nanoparticles in Medicine and Pharmacy, pg. 125-148, (M. Donbrow, ed.) CRC Press, Boca Rotan, Fla. (1991); incorporated herein by reference).

The pharmaceutical compositions described herein may be presented in unit-dose or multi-dose containers, such as sealed ampoules or vials. Such containers are typically sealed in such a way to preserve the sterility and stability of the formulation until use. In general, formulations may be stored as suspensions, solutions or emulsions in oily or aqueous vehicles, as indicated above. Alternatively, a pharmaceutical composition may be stored in a freeze-dried condition requiring only the addition of a sterile liquid carrier immediately prior to use.

8. Use of Antibodies and Other Agents

8.1 Therapeutic Use of Antibodies and Small Molecules

Methods of immunotargeting cancer cells using antibodies or antibody fragments are well known in the art. U.S. Pat. No. 6,306,393 describes the use of anti-CD22 antibodies in the immunotherapy of B-cell malignancies, and U.S. Pat. No. 6,329,503 describes immunotargeting of cells that express serpentine transmembrane antigens. Antibodies described herein (including humanized or human monoclonal antibodies or fragments or other modifications thereof, optionally conjugated to cytotoxic agents) can be introduced into a patient such that the antibody binds to cancer cells or their secreted expression products and mediates the destruction of the cells and the tumor and/or inhibits the growth of the cells or the tumor. Without intending to limit the disclosure, mechanisms by which such antibodies can exert a therapeutic effect may include complement-mediated cytolysis, antibody-dependent cellular cytotoxicity (ADCC), modulating the physiologic function of the tumor antigen, inhibiting binding or signal transduction pathways, modulating tumor cell differentiation or proliferation, altering tumor angiogenesis factor profiles, modulating the secretion of immune stimulating or tumor suppressing cytokines and growth factors, modulating cellular adhesion, and/or by inducing apoptosis. The antibodies can also be conjugated to toxic or other therapeutic agents, such as radioligands or cytosolic toxins, discussed in detail above, and may also be used therapeutically to deliver the toxic or therapeutic agent directly to tumor cells.

In preferred embodiments, the compositions have applications to the treatment of conditions or diseases involving myeloid cells of the hematopoietic system. The present disclosure further provides methods of using the antibodies to target myeloid leukemic stem cells. For example, the disclosure provides methods of using the antibodies to treat disorders involving cells of the myeloid lineages. Various diseases have origins in the committed progenitor cell populations, or involve progenitor cells by differentiation of diseased cells through the myeloid pathway.

By "treatment" herein is meant therapeutic or prophylactic treatment, or a suppressive measure for the disease, disorder or undesirable condition. Treatment encompasses administration of the subject antibodies in an appropriate form prior to the onset of disease symptoms and/or after clinical manifestations, or other manifestations, of the disease to reduce disease severity, halt disease progression, or eliminate the disease. Prevention of the disease includes prolonging or delaying the onset of symptoms of the disorder or disease, preferably in a subject with increased susceptibility to the disease.

The antibodies described herein are particularly applicable to the treatment of myeloproliferative disorders, also referred to generally as hematopoietic malignancies, which are proliferative disorders involving cells of the myeloid lineage. The term malignancy refers to growth and proliferation of one or more clones of abnormal cells. Leukemia typically describes a condition in which abnormal cells are present in the bone marrow and peripheral blood. Myeloproliferative disorders, also called myeloid leukemias or myelogenous leukemias, are categorized into three general groups of conditions; dysmyelopoietic disorder, acute myeloproliferative leukemia, and chronic myeloproliferative disorder.

Myelodysplastic Syndromes (MDS) include a group of closely-related blood formation disorders, in which the bone marrow shows qualitative and quantitative changes suggestive of a preleukemic process, but having a chronic course that does not necessarily terminate as acute leukemia. A variety of terms, including preleukemia, refractory anemia, refractory dysmyelopoietic anemia, smoldering or subacute leukemia, dysmyelopoietic syndrome (DMPS), and myelodysplasia, have all been used to describe MDS. These conditions are all characterized by a cellular marrow with impaired maturation (dysmyelopoiesis) and a reduction in the number of blood cells. DMPS is characterized by presence of megablastoids, megakaryocyte dysplasia, and an increase in number of abnormal blast cells, reflective of enhanced granulocyte maturation process. Patients with DMPS show chromosomal abonormalities similar to those found in acute myeloid leukemia and progress to acute myeloid leukemia in a certain fraction of afflicted patients (Kardon, N. et al., Cancer 50(12): 2834-2838 (1982)).

Acute myeloproliferative leukemia (AML), also known as acute nonlymphocytic leukemia, acute myelocytic leukemia, acute myeloblastic leukemia, and acute granulocytic leukemia, is characterized by the presence of abnormal hematopoietic progenitor cells that have been blocked at an undifferentiated or partially differentiated stage of maturation, and thus are unable to differentiate into myeloid, erythroid, and/or megakaryocytic cell lines. The abnormal cells block differentiation of normal progenitor cells in the bone marrow, resulting in thrombocytopenia, anaemia, and granulocytopenia. Diagnosis of AML is made when at least 30% of nucleated cells in the bone marrow are blasts. Acute myeloid leukemia is further divided into subtypes M1 to M7 based on morphology of the proliferating cells and cytochemical staining properties.

Chronic myeloproliferative disorders are a collection of conditions characterized by increased number of mature and immature granulocytes, erythrocytes, and platelets. Chronic myeloproliferative disorders can transition to other forms within this group, with a tendency to terminate in acute myeloid leukemia. Specific diseases within this group include polycythemia vera, chronic myeloid leukemia, agnogenic myeloid leukemia, essential thrombocythemia, and chronic neutrophilic leukemia.

The therapeutic preparations can use non-modified marker specific antibodies or antibodies conjugated with a therapeutic compound, such as a toxin or cytotoxic molecule, depending on the functionality of the antibody. Generally, when non-modified antibodies are used, they will typically have a functional Fc region. By "functional Fc region" herein is meant a minimal sequence for effecting the biological function of Fc, such as binding to Fc receptors, particularly FcγR (e.g., FcγRI, FcγRII, and FcγRIII). Without being bound by theory, it is believed that the Fc region may affect the effectiveness of anti-tumor monoclonal antibodies by binding to Fc receptors immune effector cells and modulating cell mediated cytotoxicity, endocytosis, phagocytosis, release of inflammatory cytokines, complement mediated cytotoxicity, and antigen presentation. In this regard, polyclonal antibodies, or mixtures of monoclonals, will be advantageous because they will bind to different epitopes (of a single antigen or of different antigens corresponding to different cytokine receptors) and thus have a higher density of Fc on the cell surface as compared to when a single monoclonal antibody is used. Of course, to enhance their effectiveness in depleting targeted cells, or where non-modified antibodies are not therapeutically effective, antibodies conjugated to toxins or cytotoxic agents may be used. Thus, not only are the antibodies useful as therapeutic molecules themselves, they also find utility in targeted delivery of therapeutic molecules to myeloid cells.

Alternatively, where the antibodies exhibit a direct effect on antigen and/or cell function, enhancement of the Fc receptor functionality may be less significant. For example, this may be the case where binding of the marker specific antibody sterically inhibits interaction between antigen and its corresponding ligand.

The antibody compositions may be used either alone or in combination with other therapeutic agents to increase efficacy of traditional treatments for myeloid leukemias, or to target abnormal cells not targeted by the antibodies. Combining the antibody therapy method with a chemotherapeutic, radiation or surgical regimen may be preferred in patients that have not received chemotherapeutic treatment, whereas treatment with the antibody therapy may be indicated for patients who have received one or more chemotherapies. Additionally, antibody therapy can also enable the use of reduced dosages of concomitant chemotherapy, particularly in patients that do not tolerate the toxicity of the chemotherapeutic agent very well. Furthermore, antibody treatment of cancer patients with tumors resistant to chemotherapeutic agents might induce sensitivity and responsiveness to these agents in combination.

In one aspect, the antibodies are used adjunctively with therapeutic cytotoxic agents, including, by way of example and not limitation, busulfan, thioguanine, idarubicin, cytosine arabinoside, 6-mercaptopurine, doxorubicin, daunorubicin, etoposide, and hydroxyurea. Other agents useful as adjuncts to antibody therapy are compounds directed specifically to an abnormal cellular molecule found in the disease state. These agents can be disease specific. For example, for treating chronic myeloid leukemia arising from BCR-ABL activity, one class of useful compounds are inhibitors of abl kinase activity, such as Imatinib, an inhibitor of bcr-abl kinase, and antisense oligonucleotides against bcr (e.g., Oblimersen). Other agents include, among others, interferon-alpha, humanized anti-CD52, deacetylase inhibitor FR901228 (depsipeptide), and the like.

In another aspect, isotopes are attached to the antibodies and/or fragments for therapeutic purposes. By "isotope" is meant atoms with the same number of protons and hence of the same element but with different numbers of neutrons (e.g., 1H vs. 2H or D). The term "isotope" includes "stable isotopes", e.g. non-radioactive isotopes, as well as "radioactive isotopes", e.g. those that decay over time, and radioactive radionuclides. In one embodiment, the antibodies and/or fragments are labeled with a radioisotope, which are useful in radioimmunotherapy. Suitable radioisotopes include without limitation an alpha-emitter, a beta-emitter, and an Auger electron-emitter (Behrt, T. et al., (2000). Eur, J. Nuclear Med. vol. 27 (7):753-765; Vallabhajosula, S. et al., J. Nucl. Med. (2005) April; 46(4):634-41). Such radioisotopes include without limitation [65]Zinc, [140]neodymium, [177]lutetium, [179] lutetium, [176 m]lutetium, [67]gallium, [159]gallium, [161] terbium, [153]samarium, erbium, [175]ytterbium, [161]holmium, [166]holmium, [167]thulium, [142]praseodymium, [143]praseodymium, [145]praseodymium, [149]promethium, [150]europium, [165]dysprosium, [111]indium, [131] iodine, [125]iodine, [123]iodine, [88]yttrium and [90]yttrium. Suitable radioactive radionuclides include without limitation, $^{67}$Cu, $^{90}$Y, $^{125}$I, $^{131}$I, $^{186}$Re, $^{188}$Re, $^{211}$At, $^{212}$Bi. These and other uses of the antibodies will be apparent to those of ordinary skill in the art in light of the disclosures provided herein.

Known small molecule agonists or antagonists can also find use in methods of treating of one or more of the myelogenous hematological proliferative disorders described above. Generally, the methods comprise administration of a therapeutically effective amount of the small molecule (or mixture of small molecules). Similarly as detailed above with respect to immunotherapies, the therapeutic composition can use the non-modified small molecule or, optionally, the small molecule is conjugated to a toxin or cytotoxic molecule or growth inhibitory agent. For example, the small molecule may be conjugated to a maytansinoid or calicheamicin, an antibiotic, a radioactive isotope, a nucleolytic enzyme, or the like.

Binding of the small molecule to a HTC of myeloid origin preferably induce cell death. Cell death may be mediated by the conjugated cytotoxic molecule or by the physiological response induced by the binding of the small molecule itself 8.1.1. Administration and Dosages The amount of the compositions needed for achieving a therapeutic effect will be determined empirically in accordance with conventional procedures for the particular purpose. Generally, for administering the compositions ex vivo or in vivo for therapeutic purposes, the compositions are given at a pharmacologically effective dose. By "pharmacologically effective amount" or "pharmacologically effective dose" is meant an amount sufficient to produce the desired physiological effect or amount capable of achieving the desired result, particularly for treating or retreating the disorder or disease condition, including reducing or eliminating one or more symptoms or manifestations of the disorder or disease. As an illustration, administration of antibodies to a patient suffering from a myeloproliferative disorder provides a therapeutic benefit not only when the underlying disease is eradicated or ameliorated, but also when the there is a decrease in the severity or duration of the symptoms associated with the disease. Therapeutic benefit also includes halting or slowing the progression of the underlying disease or disorder, regardless of whether improvement is realized.

The amount administered to the subject will vary depending upon the agent being administered, the purpose of the administration, such as prophylaxis or therapy, the state of the subject, the manner of administration, the number of administrations, the intervals between administrations, and the like. These can be determined empirically by those skilled in the art and may be adjusted based on the extent of the therapeutic response. Factors to consider in determining an appropriate dose include, but are not limited to, size and weight of the subject, the age and sex of the subject, the severity of the symptoms, the stage of the disease, method of delivery of the agents, half-life of the agents, efficacy of the agents, and what other therapy regimes have been or will be administered. Stage of the disease to consider includes whether the disease is acute or chronic, relapsing or remitting phase, as well as the progressiveness of the disease. Determining the dosages and times of administration for a therapeutically effective amount are well within the skill of the ordinary person in the art, in light of the disclosures provided herein.

For any compositions of the present disclosure, the therapeutically effective dose is readily determined by methods well known in the art. For example, an initial effective dose can be estimated from cell culture or other in vitro assays. For example, Sliwkowsky, M. X. et al., Semin. Oncol. 26(suppl. 12) 60-70 (1999) describes in vitro measurements of antibody dependent cellular cytotoxicity. A dose can then be formulated in animal models to generate a circulating concentration or tissue concentration, including that of the ICM as determined by the cell culture assays. A suitable animal model for leukemia is described in detail in the Examples below.

In addition, the toxicity and therapeutic efficacy are generally determined by cell culture assays and/or experimental animals, typically by determining a $LD_{50}$ (lethal dose to 50% of the test population) and $ED_{50}$ (therapeutically effectiveness in 50% of the test population). The dose ratio of toxicity and therapeutic effectiveness is the therapeutic index. Preferred are compositions, individually or in combination, exhibiting high therapeutic indices. Determination of the effective amount is well within the skill of those in the art, particularly given the detailed disclosure provided herein. Guidance is also found in standard reference works, for example Fingl and Woodbury, General Principles In: The Pharmaceutical Basis of Therapeutics pp. 1-46 (1975), and the references cited therein.

To achieve an initial tolerizing dose, consideration is given to the possibility that the antibodies may be immunogenic in humans and in non-human primates. The immune response may be biologically significant and may impair the therapeutic efficacy of the antibody even if the antibody is partly or chiefly comprised of human immunoglobulin sequences such as, for example, in the case of a chimeric or humanized antibody. Within certain embodiments, an initial high dose of antibody is administered such that a degree of immunological tolerance to the therapeutic antibody is established. The tolerizing dose is sufficient to prevent or reduce the induction of an antibody response to repeat administration of the marker specific antibody. Preferred ranges for the tolerizing dose are between 10 mg/kg body weight to 50 mg/kg body weight, inclusive. More preferred ranges for the tolerizing dose are between 20 and 40 mg/kg, inclusive. Still more preferred ranges for the tolerizing dose are between 20 and 25 mg/kg, inclusive.

Within these therapeutic regimens, the therapeutically effective dose of antibodies is preferably administered in the range of 0.1 to 10 mg/kg body weight, inclusive. More preferred second therapeutically effective doses are in the range of 0.2 to 5 mg/kg body weight, inclusive. Still more preferred therapeutically effective doses are in the range of 0.5 to 2 mg/kg, inclusive. Within alternative embodiments, the subsequent therapeutic dose or doses may be in the same or different formulation as the tolerizing dose and/or may be administered by the same or different route as the tolerizing dose.

For the purposes of this invention, the methods of administration are chosen depending on the condition being treated, the form of the subject antibodies or other agents, and the pharmaceutical composition. Administration of the antibody compositions or small molecule compositions can be done in a variety of ways, including, but not limited to, continuously, subcutaneously, intravenously, orally, topically, transdermal, intraperitoneal, intramuscularly, and intravesically. For example, microparticle, microsphere, and microencapsulate formulations are useful for oral, intramuscular, or subcutaneous administrations. Liposomes and nanoparticles are additionally suitable for intravenous administrations. Administration of the pharmaceutical compositions may be through a single route or concurrently by several routes. For instance, intraperitoneal administration can be accompanied by intravenous injections. Preferably the therapeutic doses are administered intravenously, intraperitonealy, intramuscularly, or subcutaneously. In some embodiments, the small molecule compositions can be administered orally.

The compositions may be administered once or several times. In some embodiments, the compositions may be administered once per day, a few or several times per day, or even multiple times per day, depending upon, among other things, the indication being treated and the judgment of the prescribing physician.

Administration of the compositions may also be achieved through sustained release or long-term delivery methods, which are well known to those skilled in the art. By "sustained release or" "long term release" as used herein is meant that the delivery system administers a pharmaceutically therapeutic amount of subject agents for more than a day, preferably more than a week, and most preferable at least about 30 days to about 60 days, or longer. Long term release systems may comprise implantable solids or gels containing the antibodies, such as biodegradable polymers described above (Brown, D. M. et al., Anticancer Drugs 7: 507-513 (1996)); pumps, including peristaltic pumps and fluorocarbon propellant pumps; osmotic and mini-osmotic pumps; and the like.

The method of the invention contemplates the administration of marker specific monoclonal antibodies, as well as combinations of different mAbs. As discussed above, two or more monoclonal antibodies may provide an improved effect compared to a single antibody. For example, a combination of a monoclonal antibody with another monoclonal antibody that binds a different antigen, e.g., an antigen corresponding to a different cytokine receptor, may provide an improved effect compared to a single antibody. Such mAb "cocktails" may have certain advantages in as much as they contain mAbs, which exploit different effector mechanisms or combine directly cytotoxic mAbs with mAbs that rely on immune effector functionality. Specific mAbs in combination may exhibit synergistic therapeutic effects. Some methods of the invention also contemplate administration of one or more known small molecule agonists or antagonists, alone or in combination with one or more mAbs described herein. The small molecule in combination with specific mAbs may exhibit synergistic therapeutic effects.

8.2 Diagnostic Use of Antibodies and other Agents

The present invention further provides methods to identify the presence of an antigen using the compositions of the present invention, optionally conjugated or otherwise associated with a suitable label. Such methods comprise incubating a test sample with one or more of the marker specific antibodies of the present invention and assaying for antibodies that bind to components within the test sample. Conditions for incubating the antibody with a test sample may vary. Incubation conditions depend on the format employed, the detection methods employed, and the antibody used in the assay. One skilled in the art will recognize that any one of the commonly available immunological assay formats can readily be adapted to employ antibodies of the present invention (see Chard, T., An Introduction to Radioimmunoassay and Related Techniques, Elsevier Science Publishers, Amsterdam, The Netherlands (1986); Bullock, G. R. et al., Techniques in Immunocytochemistry, Academic Press, Orlando, Fla. Vol. 1 (1982), Vol. 2 (1983), Vol. 3 (1985); Tijssen, P., Practice and Theory of immunoassays: Laboratory Techniques in Biochemistry and Molecular Biology, Elsevier Science Publishers, Amsterdam, The Netherlands (1985).

The sample to be assessed can be any sample that contains an expression product (e.g., RNA transcript or extracellular protein). A "test sample" generally refers to a sample obtained or derived from a patient afflicted with, or suspected of being afflicted with, a hematological proliferative disorder of myeloid origin. The test samples of the present invention include cells, protein or membrane extracts of cells, or biological fluids. Samples can comprise brain, blood, serum, plasma, lymphatic fluid, bone marrow, plasma, lymph, urine, tissue, mucus, sputum, saliva or other cell samples. The test sample used will vary based on the assay format, nature of the detection method and the tissues, cells or extracts used and the sample to be assayed. Methods for preparing protein extracts or membrane extracts of cells are well known in the art and can be readily adapted in order to obtain a sample which is compatible with the system utilized.

In preferred embodiments, the test sample is obtained from peripheral blood, particularly from mobilized peripheral blood (MPB). The sample initially obtained from a subject is generally enriched for stem cells. Hematopoietic stem cells can be identified by the presence or absence of certain surface markers, as described above, including, e.g., $CD34^+$; $CD38^-$; as well as $Lin^-$ and/or $CD90^+$.

The present invention provides diagnostic methods for hematological proliferative disorders of myeloid origin, where the level of an expression product of one or more of the disclosed cytokine receptors is detected. "Detected," and its grammatical variations, refers to assessing, measuring, reading, or otherwise determining a value for the level or amount of expression product corresponding to one or more of the cytokine receptors disclosed herein. An expression product "corresponds to" a designated cytokine receptor when it is derived therefrom via transcription and/or translation of the gene encoding the designated cytokine receptor. Expression levels refer to the amount of expression of the expression product, as described herein. A value for an expression level is also referred to as a "signal." The values for expression levels can be absolute or relative values, e.g., values provided in comparison to control levels. The values for expression levels can be raw values, or values that are optionally rescaled, filtered and/or normalized. The approach used will depend, for example, on the nature of the expression product (e.g., RNA or polypeptide) as well as specific characteristics of the product, and the intended use for the data.

For example, in one embodiment, the expression product is a transcription product, such as RNA. RNA includes, e.g, mRNA rRNA, tRNA, snRNA, and the like, including any nucleic acid molecule that is transcribed from a gene. The nucleic acid molecule levels measured can be derived directly from the gene or, alternatively, from a corresponding regulatory gene or regulatory sequence element. Additionally, variants of genes and gene expression products including, for example, spliced variants and polymorphic alleles, can be detected.

Methods of detecting the level of an RNA transcript include, for example, utilizing a specific hybridization probe or an array of such probes. In a preferred embodiment, the probe comprises a polynucleotide sequence that can hybridize to all or a portion of the transcribed RNA sequence.

The stringency conditions allowing hybridization can be high to moderate to low. As used herein, conditions of moderate stringency refer to those known to the ordinarily skilled artisan, e.g., as defined by Sambrook et al. Molecular Cloning: A Laboratory Manual, 2 ed. Vol. 1, pp. 1.101-104, Cold Spring Harbor Laboratory Press, (1989). Moderate stringency conditions include use of a prewashing solution for nitrocellulose filters 5×SSC, 0.5% SDS, 1.0 mM EDTA (pH 8.0), hybridization conditions of 50% formamide, 6×SSC at 42° C. (or other similar hybridization solution, such as Stark's solution, in 50% formamide at 42° C.), and washing conditions of about 60° C., 0.5×SSC, 0.1% SDS. High stringency conditions usually involve, for example, hybridization conditions as above, with washing at 68° C., 0.2×SSC, 0.1% SDS. The skilled artisan will recognize that the temperature and wash solution salt concentration can be adjusted as necessary according to factors such as the length of the probe. The hybridization probe can be of any length and usually consists of at least about 5 nucleotides, at least about 10, at least about 15, at least about 20, or at least about 30 nucleotides. Longer lengths are suitable to lower stringency conditions.

The probe may include natural (i.e. A, G, U, C, or T) or modified bases (7-deazaguanosine, inosine, etc.). In addition, the bases in probes may be joined by a linkage other than a phosphodiester bond, so long as the bond does not interfere with hybridization. Thus, probes may be peptide nucleic acids in which the constituent bases are joined by peptide bonds rather than phosphodiester linkages.

In some embodiments, more than one hybridization probe is used, e.g., two, three, four, five, 10 or more probes, up to, including and beyond as many probes as cytokine receptors disclosed herein. In some embodiments, different probes are directed to different RNA products, e.g., RNA products corresponding to two or more different cytokine receptors disclosed herein. For example, probes for detecting the expression level of two, three, four, five, or more of the cytokine receptor disclosed herein may be used.

In preferred embodiments, the probes are immobilized, e.g., on an array, in different known locations. An array refers to a solid support with a surface to which a plurality of different nucleic acid sequences (probes) are attached. The array can be prepared either synthetically or biosynthetically, and can assume a variety of formats, e.g., libraries of compounds tethered to resin beads, silica chips, or other solid supports, as well as libraries of nucleic acids prepared by spotting nucleic acids onto a substrate. The solid support can be any material or group of materials having a rigid or semi-rigid surface or surfaces. Generally, at least one surface of the solid support will be substantially flat, although in some case the array will include wells, raised regions, pins, etched trenches, or the like. Although a planar array surface is preferred, the array may be fabricated on a surface of virtually any shape or even a multiplicity of surfaces. Solid support(s) can also take the form of beads, resins, fibers such as fiber optics, gels, microspheres, or other geometric configurations. See U.S. Pat. Nos. 5,770,358, 5,789,162, 5,708,153, 6,040,193 and 5,800,992, which are hereby incorporated in their entirety for all purposes.

Such arrays are generally termed "microarrays", or colloquially "chips", and have been described in the art, for example, U.S. Pat. Nos. 5,143,854, 5,445,934, 5,744,305, 5,677,195, 6,040,193, 5,424,186 and Fodor et al., Science, 251:767-777 (1991), each of which is incorporated by reference in its entirety for all purposes. These arrays may generally be produced using mechanical synthesis methods or light directed synthesis methods, which can incorporate a combination of photolithographic methods and solid phase synthesis methods. Techniques for the synthesis of these arrays using mechanical synthesis methods are described in, e.g., U.S. Pat. No. 5,384,261, incorporated herein by reference in its entirety for all purposes. Commercially available probes and arrays can be used, including, for example, Affymetrix human U133 Plus 2.0 Array.

In a preferred embodiment, the expression product is mRNA and the mRNA levels are obtained by contacting the sample with a suitable microarray, and determining the extent of hybridization of the nucleic acid in the sample to the probes on the microarray.

For example, mRNA levels can be obtained from a GeneChip™ probe array or Microarray (Affymetrix, Inc.) (U.S. Pat. Nos. 5,631,734, 5,874,219, 5,861,242, 5,858,659, 5,856, 174, 5,843,655, 5,837,832, 5,834,758, 5,770,722, 5,770,456, 5,733,729, 5,556,752, all of which are incorporated herein by reference in their entirety), and the expression levels can be calculated with software (e.g., Affymetrix GENECHIP™ software). Briefly, nucleic acids (e.g., mRNA) from a sample which has been subjected to particular stringency conditions hybridize to the probes on the chip. The nucleic acid to be analyzed (e.g., mRNA corresponding to an HTC marker) is isolated, amplified and labeled with a detectable label, (e.g., $^{32}P$ or fluorescent label) prior to hybridization to the arrays. Once hybridization occurs, the arrays are inserted into a scanner which can detect patterns of hybridization. The hybridization data are collected as light emitted from the labeled groups, which are now bound to the probe array. The probes that perfectly match the mRNA corresponding to an HTC marker produce a stronger signal than those that have mismatches. Since the sequence and position of each probe on the array are known, by complementarity, the identity of the nucleic acid applied to the probe is determined. Quantitation from the hybridization of labeled mRNA/DNA microarray can be performed by scanning the microarrays to measure the amount of hybridization at each position on the microarray. This can be performed with, for example, an Affymetrix scanner (Affymetrix, Santa Clara, Calif.). Microarrays are only one method of detecting RNA levels. Other methods known in the art or developed in the future can be used with the present invention.

In another embodiment, the expression product is a translation product, e.g. one or more cytokine receptors disclosed herein. Cytokine receptor proteins include any polypeptide or derivative thereof, including, e.g., peptides, glycoproteins, lipoproteins and nucleic acid-protein complexes.

Techniques for protein detection and quantitation are known in the art. For example, antibodies specific for the protein or polypeptide can be obtained using methods which are routine in the art, and the specific binding of such antibodies to protein or polypeptide expression products can be detected and measured. Methods of detecting the level of proteins preferably involve utilizing antibodies of the instant disclosure, as discussed above. In some embodiments, small molecules known to bind to a polypeptide corresponding to a disclosed cytokine receptor can similarly be detectably labeled and/or attached to a solid support.

In some embodiments, more than one antibody is used, e.g., two or more mAbs. In some embodiments, different mAbs are directed to a proteinaceous product expressed from two or more different cytokine receptors disclosed herein. For example, antibodies for detecting the expression level of two, three, four, five, or more of the different cytokine receptors disclosed herein may be used. In some embodiments, both RNA and protein levels are detected in a given sample or multiple samples from an individual.

The RNA or antigen level can be compared to control levels, e.g., levels obtained using normal HSCs. A control sample comprising one or more normal HSCs can be obtained, e.g., from an individual not afflicted with a hematological proliferative disorder, e.g., not afflicted with a hematological proliferative disorder of myeloid origin. Preferably, the control sample is obtained in a manner similar to that used to obtain the test sample, e.g, being obtained from the same organs, tissues or fluids (as detailed above with respect to test samples); and sorted to enrich for corresponding cell types. Similarly, the level of RNA or antigen preferably is assesed in the control sample in a manner similar to that used to obtain the test values. Methods are known in the art for permitting direct comparison of test and control levels, and a specific example of such comparison is detailed below in Example 1. In some embodiments, control levels are provided by previously-obtained data, such as from control samples that have been detected in prior assays; from published data; and/or from accessible data bases.

Diagnosis is based on a correlation between the level of a given expression product in a test sample compared to that in a control sample. For example, as detailed in Example 1 below, mRNA levels of the cytokine receptors disclosed herein are higher in AML HTC samples as compared to normal HSC samples. Preferably, the difference in expression levels is at least about 2 fold, at least about 3 fold, at least about 5 fold, at least about 7 fold, at least about 10 fold or at least about 15 fold. In particularly preferred embodiments, the difference in expression levels is at least about 20 fold, at least about 30 fold, at least about 40 fold or at least about 50 fold. In still more preferred embodiments, the difference in expression levels is at least about 70 fold, at least about 100 fold, at least about 200, fold or as much as nearly 300 fold, 400 fold or 500 fold. For example, IL13RA1 mRNA levels in AML HTCs is over 35 times that in normal HSCs (see Table 1). Accordingly, the information provided by the present disclosure, alone or in conjunction with other test results, aids in sample classification and diagnosis of hematological proliferative disorders of myeloid origin, such as AML.

In some embodiments, more than one test sample and/or more than one control sample are obtained and/or detected. For example, as illustrated in Example 1 below, all of 3 normal samples showed low levels of expression of each cytokine receptor, while at least 2 out of 3 AML samples showed high expression levels. Alternatively, AML samples over-expressed the cytokine receptor by at least about 5 fold compared to normal HSCs. Diagnosis may take into account the difference in expression levels between more than one test sample and/or more than one control sample. In some embodiments, repeat assays are performed using a given sample.

In some embodiments, expression of more than one cytokine receptor can be detected. The different cytokine receptors can be detected simultaneously. For example, in some embodiments, two, three, four, five, or more of the different cytokine receptors disclosed herein are detected. The detection of numerous genes can provide a more accurate evaluation of the sample. The correlation between expression product levels and a given disease, such as AML, can be determined using a variety of methods. Methods of classifying samples are described, for example, in U.S. patent application Ser. No. 09/544,627, filed Apr. 6, 2000 by Golub et al., the teachings of which are incorporated herein by reference in their entirety.

The present invention also provides prognostic methods for predicting the efficacy of treating a haematological proliferative disorder of myeloid origin, where the level of an expression product of one or more of the disclosed cytokine receptors is detected and wherein the expression product level is correlated with a treatment outcome. "Treatment outcome" as used herein refers to the efficacy of a treatment with respect to a disease, that is, the response of the disease to a particular treatment. The levels of expression products can be used to assess the likelihood that a given disorder will respond well to a particular treatment, or to determine which of a number of treatment options is more preferable. In some embodiments, the treatment is one disclosed herein, e.g., one or more of the therapeutic uses of the antibodies described herein. In some embodiments, the treatment is a treatment otherwise known or used or to be used in the art; or a combination of such treatments with one or more of those disclosed herein.

The disclosure above regarding, for example, test and control samples; stem cell sorting; use of one or more cytokine receptors; detection of RNA and/or antigen levels; correlation of data and so forth, as provided in the case of diagnostic methods, also applies to the prognostic methods disclosed herein.

In a preferred embodiment, the expression product is RNA and RNA levels in test samples are compared to control levels. In a particularly preferred embodiment, the expression product is mRNA and the mRNA levels are obtained by contacting the sample with a suitable microarray, and determining the extent of hybridization of the nucleic acid in the sample to the probes on the microarray.

In particularly preferred embodiments, the expression product is mRNA and lower mRNA levels correlate with more favorable treatment outcomes. For example, a TRGV9 expression level that is about 10 times higher than control levels indicates a more favorable outcome than where the TRGV9 expression level is about 30 times higher. In some embodiments, the expression levels of more than one cytokine receptor is be detected; and lower expression levels of multiple markers is further indication of a more favorable treatment outcome.

The present invention also provides methods for monitoring the efficacy of treating a haematological proliferative disorder of myeloid origin, where the level of an expression product of one or more of the disclosed cytokine receptors is detected at various time points and correlated with treatment outcome. The various time points can include, for example, time of diagnosis, times prior to commencing a treatment regime; times at intervals during a treatment regime; and times after the conclusion of treatment regime. The time intervals can include several hours; a day; 2, 3, or 4 days; a week; 2, 3, 4, 5 or 6 weeks; a month, 2, 3, 4, 5, or 6 months, a year, or several years post-initiation of a treatment regime. In some embodiments, the treatment is one disclosed herein, e.g., one or more of the therapeutic uses of the antibodies described herein. In some embodiments, the treatment is a treatment otherwise known or used or to be used in the art; or a combination of such treatments with one or more of those disclosed herein.

The disclosure above regarding, for example, test and control samples; stem cell sorting; use of one or more cytokine receptors; detection of RNA and/or protein levels; correlation of data and so forth, as provided in the case of diagnostic methods, also applies to the monitoring methods disclosed herein.

In a preferred embodiment, the expression product is RNA and RNA levels in test samples are compared to control levels. In a particularly preferred embodiment, the expression product is mRNA and the mRNA levels are obtained by contacting the sample with a suitable microarray, and determining the extent of hybridization of the nucleic acid in the sample to the probes on the microarray.

Monitoring the efficacy of a treatment is useful, e.g., in facilitating clinical management of the disease, e.g., where decisions must be made as to whether to continue a treatment course or advance to other treatment options. Whether a myeloid leukemia is responding positively to a treatment can be determined based on changes in the level of a given expression product (or products) in test samples taken at various time points, e.g., before and after administration of a particular treatment.

A shift in expression product levels from a level correlated with HTCs of myeloid origin towards a level correlated with normal HSCs is evidence of an effective therapeutic regime. In some embodiments, a reduction in the expression product level corresponding to one or more of the cytokine receptors disclosed herein indicates a positive response to treatment. The reduction indicates a trend towards levels seen in normal HSC samples. For example, as detailed in Example 1 below, the expression product level in AML HTCs is higher than that in normal HSCs for each of the cytokine receptors disclosed herein. A reduction in expression level in one or more of the disclosed cytokine receptors, e.g., in test samples obtained after the commencement of treatment, would indicate a positive response.

In preferred embodiments, the expression level for one or more HTC markers is reduced at least about 5 fold, at least about 7 fold, at least about 10 fold or at least about 15 fold, during the course of treatment. In particularly preferred embodiments, the expression level for one or more HTC markers is reduced at least about 20 fold, at least about 30 fold, at least about 40 fold or at least about 50 fold, during the course of treatment. In still more preferred embodiments, the expression level for one or more HTC markers is reduced at least about 70 fold, at least about 100 fold, at least about 200 fold, or as much as nearly about 300 fold, about 400 fold or about 500 fold, during the course of treatment. For example, IL5RA mRNA levels in AML HTCs is almost 750 times that in normal HSCs (see Table 1). A reduction to 200, 100, 50, 20, 10, or just 2 times the IL5RA mRNA levels in normal HSCs is evidence of an effective therapeutic regime.

In some embodiments, the methods of the present invention are suitable for diagnosis prognosis and/or monitoring of a haematological proliferative disorder of myeloid origin, such as myoproliferative disorders. The present invention also provides methods of diagnosis, prognosis and monitoring of a myoproliferative disorder that is chronic myeloid leukemia (CML) and/or acute myeloid leukemia (AML). In a particularly preferred embodiment, the myelogenous haematological proliferative disorder is AML and the level of RNA or antigen is detected using a test sample comprising AML HTCs, compared to control levels obtained from a control sample of normal HSCs.

9. Kits

In another aspect of the present invention, kits are provided which contain one or more of the necessary reagents to carry out methods of the present invention. Specifically, some embodiments provide a compartment kit having one or more containers, which comprise: (a) a first container comprising one of the marker specific antibodies or complexes of the present invention, e.g., a first monoclonal antibody that specifically binds a first antigen corresponding to one of the cytokine receptors disclosed herein; and (b) one or more other containers comprising one or more of the following: wash reagents, reagents capable of detecting presence of the antibody, and/or another marker specific antibody or complex of the present invention, e.g., a second monoclonal antibody that specifically binds a second antigen corresponding to a different cytokine receptor disclosed herein. In some embodiments, kits include additional containers, e.g., comprising third, fourth, fifth, etc., antibodies directed to antigens corresponding to a third, fourth, fifth, etc., cytokine receptor disclosed herein. In some embodiments, additional containers include one or more known small molecule agonists or antagonists that find use in the prognostic, diagnostic and/or therapeutic methods taught herein.

The kit typically contains containers which may be formed from a variety of materials such as glass or plastic, and can include, for example, bottles, vials, syringes, and test tubes. A compartment kit includes any kit in which reagents are contained in separate containers. Such containers include small glass containers, plastic containers or strips of plastic or paper. Such containers allow efficient transfer of reagents from one compartment to another compartment, such that the samples and reagents are not cross-contaminated, and the agents or solutions of each container can be added in a quantitative fashion from one compartment to another. One skilled in the art will readily recognize that the disclosed antibodies of the present invention can be readily incorporated into one of the established kit formats, which are well known in the art.

Provided herein are kits which include a composition described herein. In some embodiments the kit comprises a hybridoma, complex, antibody and/or mixtures of antibodies disclosed herein. In some embodiments, kits for therapeutic applications are provided, such as a kit housing a pharmaceutical formulation, e.g., one or more of the pharmaceutical compositions described herein. In some embodiments, the kits contain at least one additional reagent, including other antibodies, other monoclonal antibodies directed to HSCs, other agents described herein, committed progenitor cells, polyclonal antibodies, or mixtures of the antibodies as reagents for detecting myeloid cell types. Frozen or fixed forms of HSCs, CMPs, GMP and/or MEPs reactive with the antibodies and reagents form additional contents of the kits.

In some embodiments, the kit is a diagnostic kit for use in detecting test samples. The kit can include a control antibody that does not react with the antigen to be assayed, along with a marker specific antibody or antigen-binding fragment thereof which specifically binds to an antigen corresponding to a cytokine receptor disclosed herein. Further, such a kit can include a means for detecting the binding of said antibody to the antigen (for example, the antibody may be conjugated to a fluorescent compound such as fluorescein or rhodamine which can be detected by flow cytometry).

In preferred embodiments, the diagnostic kit includes a substantially isolated antibody that specifically binds an antigen corresponding to an HTC marker (e.g., a cytokine receptor disclosed herein), as well as means for detecting antigen-antibody binding. In some embodiments, the antibody is attached to a solid support. In some embodiments, the antibody is a monoclonal antibody. The detecting means of the kit can include a second, labeled monoclonal antibody. Alternatively, or in addition, the detecting means can include a labeled, competing antigen.

In one diagnostic configuration, the test sample is reacted with a solid phase reagent having a surface-bound antigen, where the antigen corresponds to one (or more) of the cytokine receptors disclosed herein. After washing to removing unbound components, the reagent can be reacted with reporter-labeled anti-human antibody to determine the amount of anti-antigen antibody bound to the solid support. Such methods are well known and have been extensively described in the art. The reporter label can be an enzyme, for example, which is detected by incubating the solid phase with a suitable fluorometric, luminescent or calorimetric substrate, as is standard in the art.

The solid surface bearing bound antigens and/or antibodies, as described above, can be prepared by known techniques for attaching protein material to solid support material. Suitable solid support materials include, for example and without limitation, polymeric beads, dip sticks, 96-well plate or filter material. In some embodiments, a small molecule known to bind to a polypeptide corresponding to a disclosed cytokine receptor can be attached to a solid support, based on its chemical structure by methods known in the art.

A text label typically accompanies the kit, and includes any writing or recorded material, which may be electronic or computer readable form (e.g., disk, optical disc, or tape) providing instructions or other information for using one or more of the contents of the kit. In some embodiments, the label indicates that the contents are used for diagnosing or treating the disorder of choice, such as a hematopoietic proliferate disorder of myeloid origin, according to one or more of the methods described herein. In some embodiments, AML represents the disorder to be diagnosed and/or treated using the contents of the kit. In some embodiments, CML represents the disorder to be diagnosed and/or treated using the contents of the kit.

10. Examples

10.1 Example 1

Identification of Cytokine Receptors Associated with HTCs

HTC markers were identified by comparing RNA transcript levels in normal HSCs and in AML CSCs for a variety of genes using micorarrays. Specifically, data was obtained for test samples comprising AML Lin$^-$CD34$^+$CD38$^-$ cells, where three AML samples were taken from peripheral blood; Lin$^-$CD34$^+$CD38$^-$ and Lin$^-$CD34$^+$CD38$^+$ cells were double sorted. The sorting strategy produced cells which were also over 90% CD90$^-$. The sorting strategy produced purities greater than 98%.

To allow for direct comparison, data was then obtained from control samples comprising normal HSCs. A sample was taken from mobilized peripheral blood (MPB) of each of three individual donors and Lin⁻CD34⁺CD90⁺CD45RA⁻CD38⁻ and Lin⁻CD34⁺CD90⁺CD45RA⁻CD38⁺ cells were double sorted. The sorting strategy produced a purity of over 99%.

Figure 2:
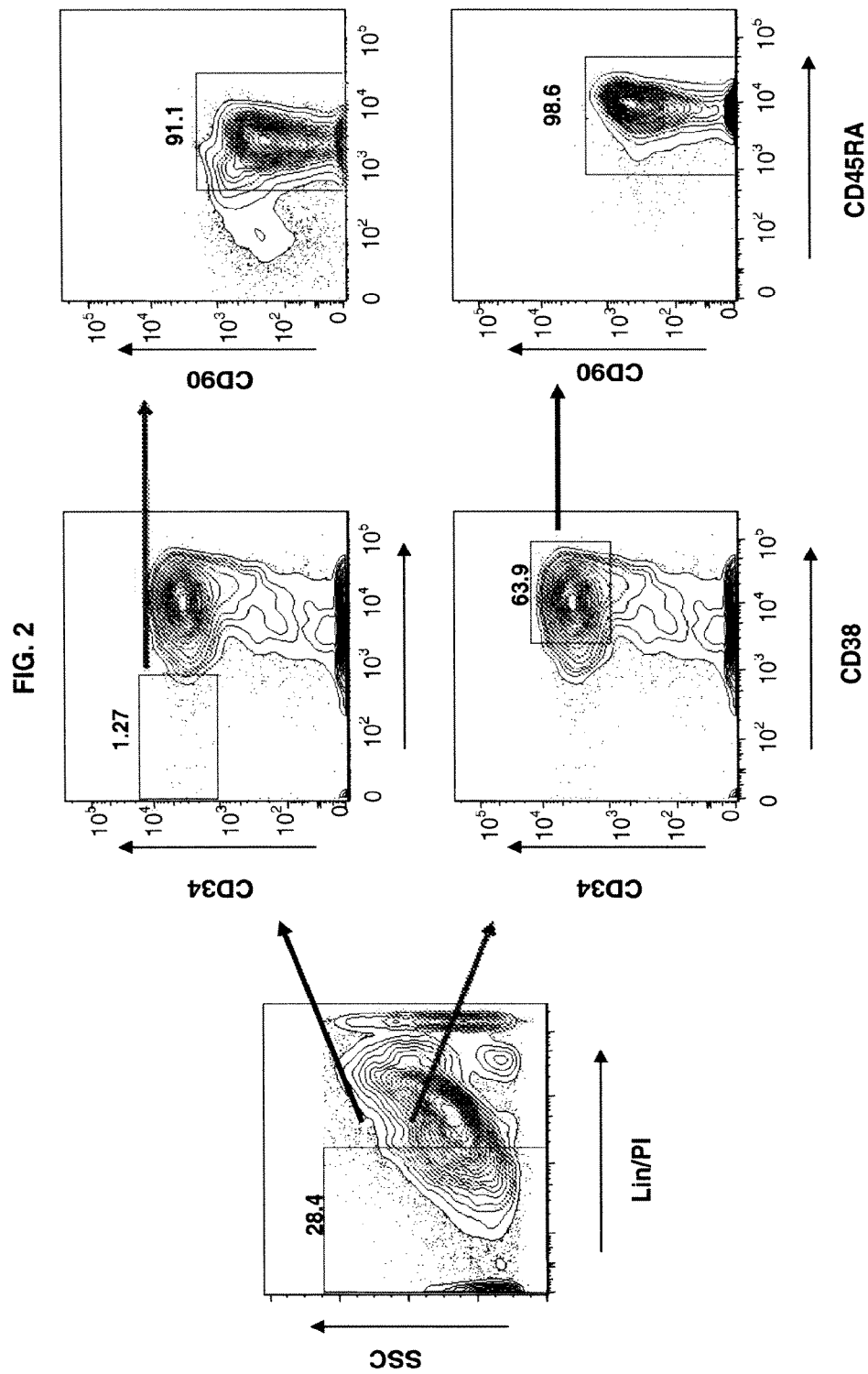
FIG. 2 shows the results of double sorting Lin–CD34+ CD90+CD45RA–CD38– and Lin–CD34+CD90+ CD45RA–CD38+ cells from 3 samples taken from peripheral blood of 3 individual patients diagnosed with AML.

For both sorting strategies, the Lineage (Lin) cocktail included antibodies against CD2, CD3, CD11b, CD15, CD19, CD41, and CD235. Exemplary dot plots of control samples and AML samples are shown in FIGS. 1 and 2, respectively.

Total RNA was then extracted, the RNA was reverse transcribed and in vitro transcribed to ultimately yield fluorochrome labeled cRNA probes from the transcripts. Transcript levels were detected using Affymetrix whole Human Genome U133 Plus 2.0 Array. Briefly, the gene array was hybridized and read out. Signal intensities, probe set ID# and absence/presence score for each probe set was tabulated using MS Excel.

The signal values corresponding to RNA transcript levels in AML test samples and control samples (Lin⁻CD34⁺CD90⁺CD45RA⁻CD38⁻ normal HSCs) were then directly compared using MS Excel and Fisher's t-test.

HTC marker genes were then selected based on the following criteria: (1) significance of signal intensity difference between test and control samples cohorts p<0.05; (2) genes not expressed in all 3 normal HSC samples (scored 'absent' by Affymetrix software); (3) genes expressed in at least 2 out of 3 AML samples (scored 'present' by Affymetrix software); (4) AML/HSC signal ratio ≥5 or 5) genes whose expression was known to be extracellular and a cytokine receptor.

Tables 1 and 2 below shows comparison for 10 genes that were over-expressed in at least 2 out of the 3 of the CD38⁻ or CD38⁺, respectively, AML CSC samples compared to all three of the normal HSC samples. "Pos. samples" refers to positive samples, scored as 'present' by Affymetrix software (in the case of normal HSCs) or giving a signal intensity greater than 25 (in the case of AML CSCs).

TABLE 1

| Gene | Normal CD38⁻ HSC sample | | CD38⁻ AML CSC sample | | |
|---|---|---|---|---|---|
| | Pos. samples detected | Average signal intensity | Pos. samples detected | Average signal intensity | Signal ratio |
| CSF1R | 0/3 | 26 | 2/3 | 89 | 3 |
| IFNAR1 | 0/3 | 30 | 2/3 | 59 | 2 |
| IL13RA1 | 0/3 | 14 | 2/3 | 467 | 33 |
| IL1RAP | 0/3 | 25 | 2/3 | 411 | 16 |
| IL5RA | 0/3 | 8 | 2/3 | 6000 | 750 |
| INSR | 0/3 | 49 | 2/3 | 132 | 3 |
| IL1RL1 | 0/3 | 18 | 2/3 | 342 | 19 |
| LTK | 0/3 | 39 | 2/3 | 126 | 3 |
| TACSTD1 | 3/3 | 189 | 2/3 | 1561 | 8 |

TABLE 2

| Gene | Normal CD38⁺ HSC sample | | CD38⁺ AML CSC sample | | |
|---|---|---|---|---|---|
| | Pos. samples detected | Average signal intensity | Pos. samples detected | Average signal intensity | Signal ratio |
| CSF1R | 0/3 | 36 | 2/3 | 193 | 5 |
| IFNAR1 | 0/3 | 23 | 3/3 | 112 | 5 |
| IL13RA1 | 3/3 | 179 | 3/3 | 606 | 3 |
| IL1RAP | 1/3 | 54 | 3/3 | 803 | 15 |
| IL5RA | 0/3 | 7 | 2/3 | 1137 | 162 |
| LILRA1 | 0/3 | 13 | 2/3 | 44 | 3 |
| INSR | 0/3 | 33 | 3/3 | 192 | 6 |
| IL1RL1 | 0/3 | 50 | 3/3 | 136 | 7 |
| LTK | 0/3 | 28 | 2/3 | 132 | 5 |
| TACSTD1 | 3/3 | 201 | 2/3 | 2474 | 12 |

Comparison of published data by Gal et al. ("Gene expression profiles of AML derived stem cells; similarity to hematopoietic stem cells." Leukemia 2006, 20: 2147-2154., incorporated herein by reference in its entirety) with control samples described herein corroborates use of CSF1R, and LTK as cancer stem cell targets (See U.S. Patent Application No. 61/039,701, incorporated herein by reference).

Figure 3:
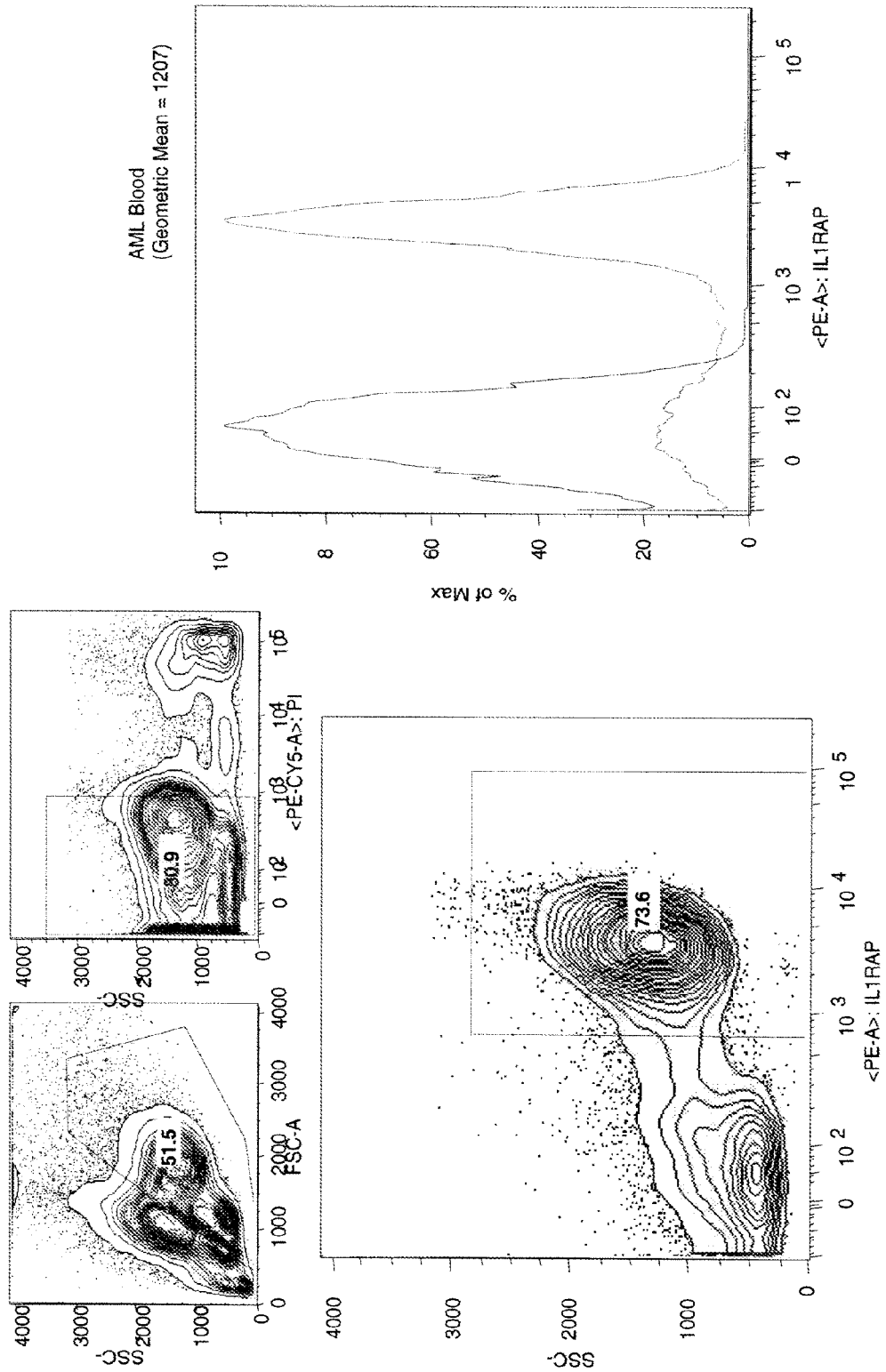
FIG. 3 shows representative results of incubating peripheral blood cells from an individual diagnosed with AML with an antibody specific for IL1RAP. The upper left panels show the gating, and bottom and right panels show IL1RAP staining.
Figure 4:
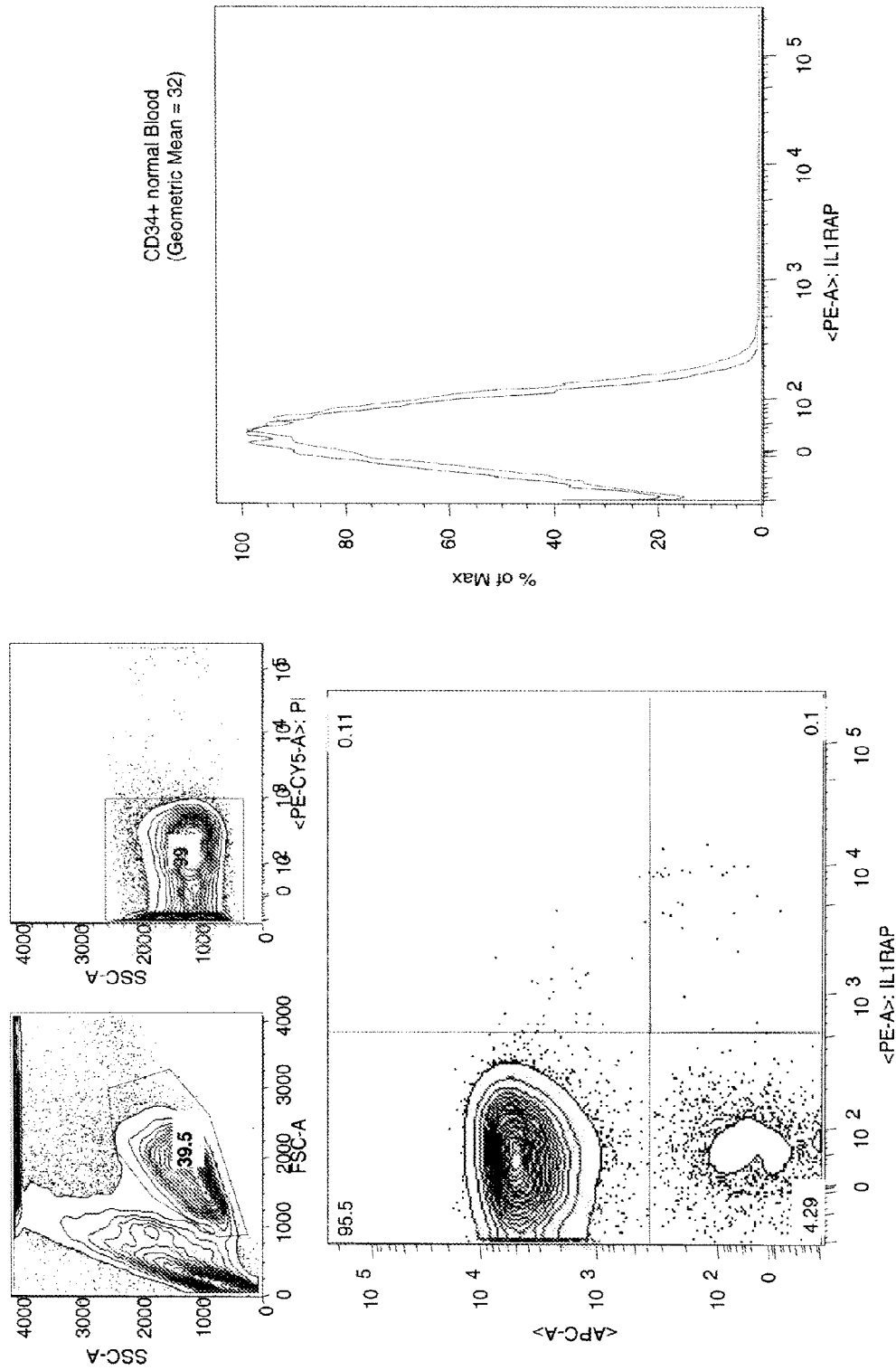
FIG. 4 shows representative results of incubating CD34+ immobilized peripheral blood from donors not afflicted with AML with an antibody specific for IL1RAP. The upper left panels show the gating, and bottom and right panels show IL1RAP staining.
Figure 5:
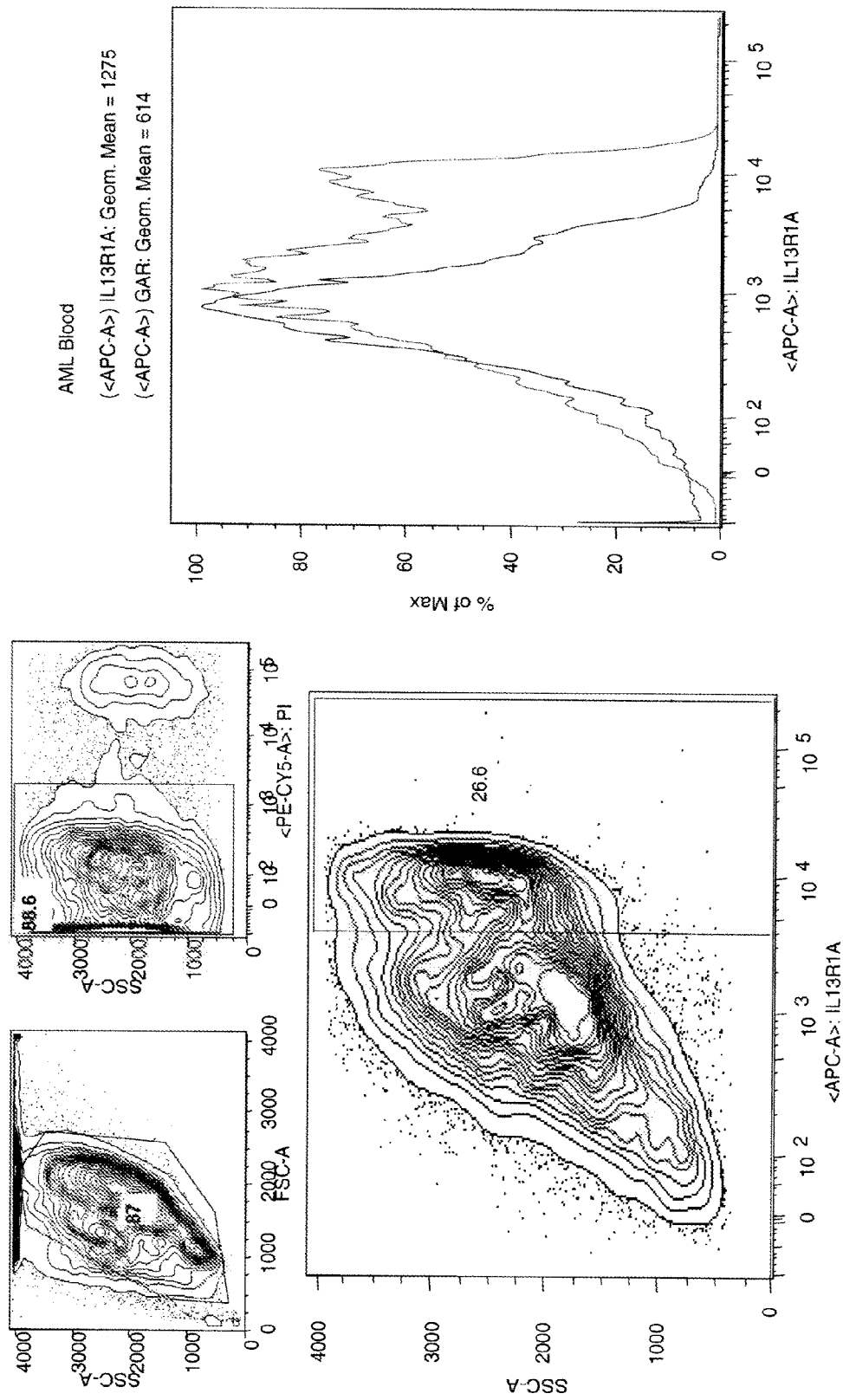
FIG. 5 shows representative results of incubating peripheral blood cells from an individual diagnosed with AML with an antibody specific for IL13R1. The upper left panels show the gating, and bottom and right panels show IL13R1 staining.
Figure 6:
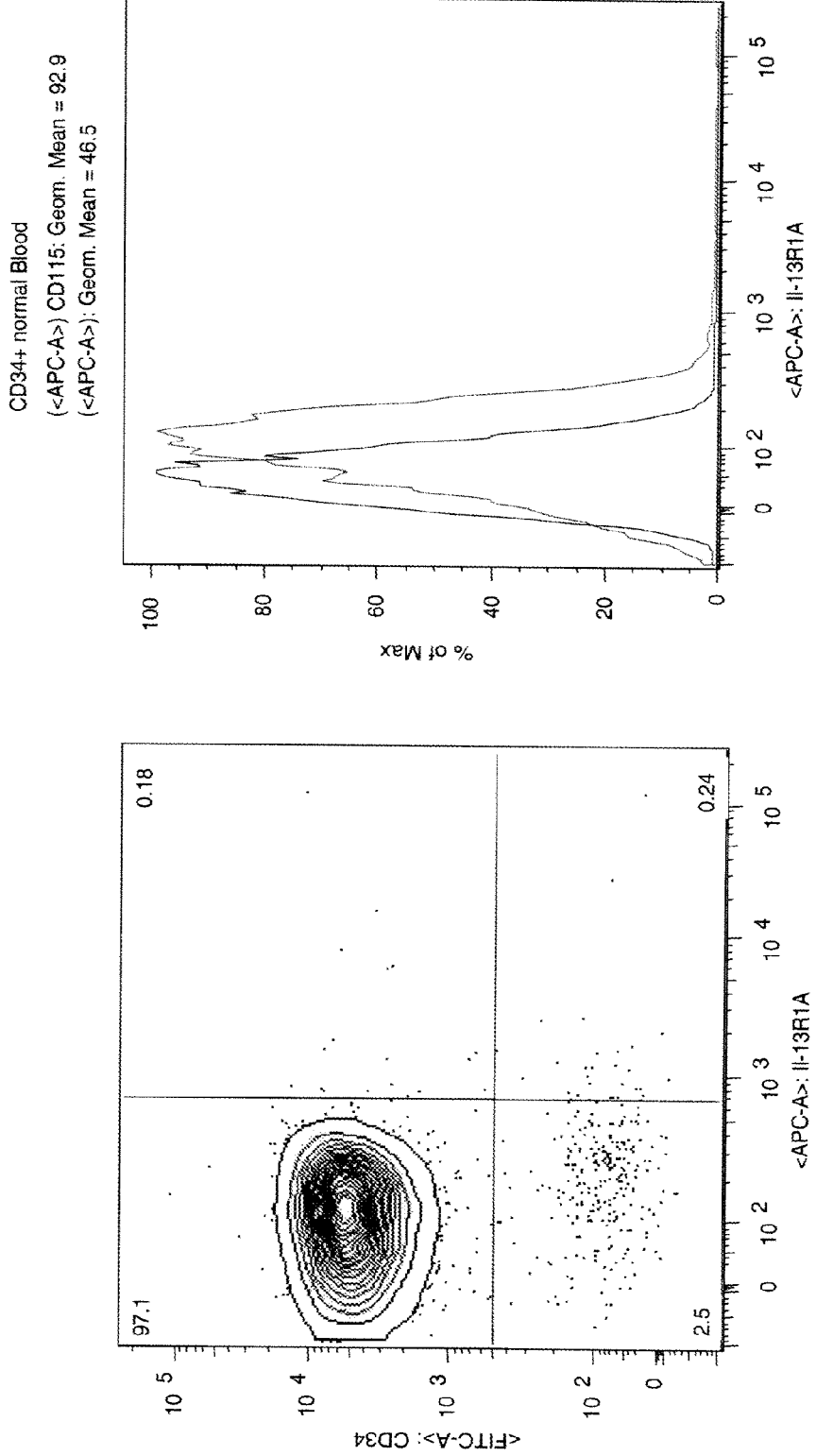
FIG. 6 shows representative results of incubating CD34+ immobilized peripheral blood from donors not afflicted with AML with an antibody specific for IL13R1. The upper left panels show the gating, and bottom and right panels show IL13R1 staining.

As shown in FIG. 3, f expression of IL1RAP by AML CSCs was detectably by flow cytometric analysis using the 3D8 antibody from Novus Biological (Littleton, Colo.). In contrast, expression of IL1RAP by normal HSCs is undetectable by flow cytometric analysis (FIG. 4).

10.2 Example 2

Production and In Vivo Efficacy of Monoclonal Antibodies 10.2.1. Preparation of Monoclonal Antibodies that Specifically Bind an Cytokine Receptor Associated with HTCs.

Techniques for producing the monoclonal antibodies are known in the art and are described, for instance, in Goding, Monoclonal Antibodies: Principles and Practice, pp. 59-103 (Academic Press, 1986). Immunogens that may be employed include a purified polypeptide corresponding to colony stimulating factor 1 receptor (CSF1R); interleukin 13 receptor, alpha 1 (IL13RA1); interleukin 1 receptor accessory protein (IL1RAP); interferon-a receptor 1 (IFNAR1); interleukin-5 receptor (IL5R); insulin receptor (INSR); interleukin 1 receptor-like 1 (IL1RL1); leukocyte receptor tyrosine (LTK); or tumor associated calcium signal transducer 1 (TACSTD1) as well as fusion proteins containing the same. Alternatively, cells expressing recombinant CSF1R; IL13RA1; IL1RAP; IFNAR1, IL5RA, INSR, IL1RL1, LTK or TACSTDI, on the cell surface, may be used. Selection of the immunogen can be made by the skilled artisan without undue experimentation.

Mice, such as Balb/c, are immunized with the selected immunogen, emulsified in complete Freund's adjuvant and injected subcutaneously or intraperitoneally in an amount from 1-100 micrograms. Alternatively, the immunogen is emulsified in MPL-TDM adjuvant (Ribi Immunochemical Research, Hamilton, Mont.) and injected into the animal's hind foot pads. The immunized mice are then boosted 10 to 12 days later with additional immunogen emulsified in the selected adjuvant. Thereafter, for several weeks, the mice may also be boosted with additional immunization injections. Serum samples may be periodically obtained from the mice by retro-orbital bleeding for testing in ELISA assays to detect antibodies directed to the HTC marker polypeptide.

After a suitable antibody titer has been detected, the animals "positive" for antibodies can be injected with a final intravenous injection of the immunogen corresponding to an HTC marker. Three to four days later, the mice are sacrificed and the spleen cells harvested. The spleen cells are then fused (using 35% polyethylene glycol) to a selected murine myeloma cell line such as P3X63AgU.1, available from ATCC, No. CRL 1597. The fusions generate hybridoma cells which can then be plated in 96 well tissue culture plates containing HAT (hypoxanthine, amininopterin, and thymidine) medium to inhibit proliferation of non-fused cells, myeloma hybrids, and spleen cell hybrids.

The hybridoma cells then can be screened in an ELISA for reactivity against the immunogen corresponding to the HTC marker. Determination of "positive" hybridoma cells secreting the desired monoclonal antibodies directed against the HTC marker polypeptide is within the skill in the art.

The positive hybridoma cells can be injected intraperitoneally into syngeneic Balb/c mice to produce ascites containing the monoclonal antibodies directed to polypeptide corresponding to the HTC marker. Alternatively, the hybridoma cells can be grown in tissue culture flasks or roller bottles. Purification of the monoclonal antibodies produced in the ascites can be accomplished using ammonium sulfate precipitation, followed by gel exclusion chromatography, as known in the art. Alternatively, affinity chromatography based upon binding of antibody to protein A or protein G can be employed, also as known in the art.

10.2.2. In Vivo Efficacy of Monoclonal Antibodies Against Myeloid Leukemia

In vivo models of human cancer are useful to determine preclinical efficacy of candidate therapeutic agents. For monoclonal antibodies, studies in appropriate animal models help evaluate target cell lysis and tumor eradication under physiological conditions in vivo. Several groups have described engraftment of CML chronic phase (CP), accelerated phase (AP), and/or blast phase (BP) and AML cells into SCID and NOD/SCID mice. In general, generation of chimeric animals showing engraftment of human CML cells is more consistent in NOD/SCID mice (See Dazzi. F et al, Blood 92: 1390-1396 (1998); Wang, J. C. Y. et al, Blood 91: 2406-2414 (1998); Dick, J et al Blood 87: 1539-1548 (1996); Bonnet, D et al, Blood 106: 4086-4092 (2005)). In vivo efficacy of monoclonal antibodies against CML and/or normal GMP and not HSC can be determined using the NOD/SCID human CML model.

Xenograft animals can be generated as described by Dazzi et al. Briefly, NOD/SCID mice are bred in house or purchased from a commercial supplier (Jackson Laboratories) and housed under pathogen-free conditions. Prior to injection of cells, animals are irradiated (250 cGy, x-ray source). Cryopreserved cells from a CML or AML patient obtained from peripheral blood, mobilized peripheral blood, or bone marrow are analyzed by flow cytometry to determine the percentage of $CD34^+$ cells in the sample. Samples containing 1 to $10 \times 10^6$ $CD34^+$ cells are injected IV into the conditioned mouse in a total volume of 1 mL. Alternatively, $CD34^+$ cells can be sorted from the sample by FACS prior to transplantation. A subset of the animals is sacrificed weekly and bone marrow and spleen analyzed for human $CD34^+$ cells.

Patient samples with engraftment potential are selected for use in antibody efficacy studies. For efficacy studies, CML/AML cells are transplanted and the test monoclonal antibody or control antibody will be injected on a schedule. Alternate schedules include once to 3 times per week, 1-3 injections per week for 1-4 weeks, or 1-2 per week for 1-4 months. Injections can be intravenous by tail vein injection, intraperitoneal, subcutaneous, or intramuscular. Following completion of the treatment schedule, animals are sacrificed and tissues collected for analysis. Peripheral blood, spleen and bone marrow can be evaluated by FACS analysis for the presence of human phenotypic CML cancer stem cells, $CD34^+$ marker$^+$ HTCs, detectable in the bone marrow and spleen at the conclusion of the treatment. Philadelphia (Ph) chromosome can be assayed by PCR to determine whether the cells are CML or normal.

As an example, eleven mice can be transplanted with CML sample (MISIRB 31104 750), $5 \times 10^6$ cells/mouse. Mice can be conditioned with 250 rad TBI (x-ray source, Faxitron CP160), and anti-asialo GM1. The anti-asialo GM1 is injected by intraperitoneal injection on days 0, 5 and 11. At 4 weeks post transplant half the mice in each group will begin receiving intraperitoneal or intravenous injections of a clone of a marker specific mAb, described herein, or control antibody, 250-1000 mg/dose, two times a week for 4 weeks. Additionally, a group of 40 mice are also transplanted with CML (MISIRB 31104 750) as above. Antibody administration begins at the time of transplant. Mice are injected by intraperitoneal injection with 0.5-1 mg/dose of antibody, twice a week for 8 weeks. Alternatively, CML cells isolated from previously engrafted mice will be serially transplanted. Some of these secondary recipients will be treated with the marker specific mAb clone at time of transplantation by intraperitoneal injection with 0.5-1 mg/dose of antibody, twice a week for 8 weeks. Following the above treatments with the marker specific mAb clone, the mice are analyzed by flow cytometry for tumor burden, expression of CD34 and expression of the specific HTC marker gene. The number and frequency of human cells in the bone marrow and spleen will be determined for all mice surviving to the end of the study. Human cells (marker+) will be sorted by FACS from both groups of mice for serial transplantation to determine if cells with functional cancer stem cell potential are present.

For secondary transplant of CML cells, $CD34^+$ marker$^+$ cells can be sorted from the bone marrow and spleen of several mice for transplantation. NOD/SCID analysis for the secondary transplant can be performed 8 or 10 weeks post transplant with the CD34 compartment of bone marrow.

Determination of Whether the Marker Specific Monoclonal Antibody Clone can Eliminate or Reduce Tumor Burden in Mice Transplanted with Primary Human AML Blast Crisis Cells.

Twenty-five mice can be transplanted with AML cells injected at $10 \times 10^6$ $CD34^+$ marker$^+$ cells/mouse. Cells are injected intravenously into the tail vein or the post lateral aspect of the orbital cavity. Mice are conditioned with 250 rad TBI (x-ray source, Faxitron CP160), and anti-asialo GM1. The anti-asialo GM1 is injected IP on days 0, 5 and 11. Beginning 4 weeks post transplant, mice are randomized into 2 groups, therapy and control. The group receiving the therapeutic is injected I.P. with the marker specific mAb clone. Antibody will be administered by intraperitoneal injection 2 times a week, for 4 weeks. Antibody concentration will be 1 mg per injection (a total of 2 mg/mouse/week). Volume will vary depending on the antibody lot used. Mouse IgG will be used as the control article; it will be prepared in the same diluent and injected at the same concentration and volume as the monoclonal antibody. Mice will be sacrificed 2-3 days following the last injection of marker specific antibody clone. Bone marrow and spleen will be isolated and counted. Tissues will be analyzed by FACS for expression of CD34 and the specific HTC marker gene. The number and frequency of human cells in the bone marrow and spleen will be determined for all mice surviving to the end of the study. Human cells will be sorted by FACS from both groups of mice for serial transplantation to determine if cells with functional cancer stem cell potential are present post-antibody treatment. Alternatively, mice will begin antibody treatment at the time of AML cell transplant. These mice will be injected with 0.5 mg of antibody 2 times a week for 8 weeks. Analysis will proceed as described above.

In addition, the efficacy of the maker specific mAb clone can be tested for efficacy in leukemia in vivo models using human cell lines expressing the corresponding antigen. Immunocompromised animals will be inoculated with human leukemia cell lines recognized by the marker specific mAb clone. The efficacy of the clone will be tested using multiple cell lines. The cell lines used should maintain a primitive phenotype in vivo with sustained expression of the epitope recognized by the marker specific mAb clone. Such cell lines will be identified and used as appropriate. Each cell line will be characterized using different routes of administration; intravenous, subcutaneous or intraperitoneal injection. NOD/SCID mice will be tested for tumor engraftment at the site of injection and subsequent invasion of bone marrow and spleen. Animals will be treated with the marker specific mAb clone beginning at the time of tumor inoculation or following tumor engraftment with injections starting 1-4 weeks post cell administration. Antibody will be administered by intraperitoneal injection 2 times a week, for 4 weeks. Mouse IgG will be used as the control article, injected at the same concentration and volume as the marker specific mAb clone. Test cells will be administered at a single site. Animals are weighed weekly and observed for clinical signs of toxicity and death for the duration of treatment. Animals are observed and palpated for the formation of nodules at the site of injection twice weekly. Detected nodules will be measured in two dimensions and findings recorded. The injection site is exposed at the end of study and tumor removed and measured and weighed. In addition, a sample of bone marrow, spleen and tumor mass are to be removed for phenotyping by FACS. These tissues will be disassociated and prepared for analysis by flow cytometry. Tissues will be screened for expression of one or more of the human HTC markers and the marker specific mAb clone.

Using the above described in vivo models, it can be shown that treatment with monoclonal antibody compositions of the present invention is effective in reducing tumor size, ameliorating one or more symptoms and/or prolonging survival of mice in the therapy group.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents.

All patents, patent applications, publications, and references cited herein are expressly incorporated by reference to the same extent as if each individual publication or patent application was specifically and individually indicated to be incorporated by reference.

What is claimed is:

1. A method of destroying a human myeloid cancer stem cell (CSC) comprising contacting the CSC with an antibody specific the interleukin 1 receptor accessory protein (IL1RAP), wherein binding of the antibody to IL1RAP mediates destruction of the CSC, and wherein the antibody is conjugated to a cytotoxic or chemotherapeutic agent.

2. The method of claim 1, wherein the CSC is an acute myeloid leukemia (AML) or chronic myeloid leukemia (CML) stem cell.

3. A method of treating myoproliferative disorder in a human subject, comprising
    administering a pharmaceutical composition comprising an antibody specific for interleukin 1 receptor accessory protein (IL1RAP) expressed on the surface of a myeloid cancer stem cell (CSC), wherein binding of the antibody to IL1RAP mediates destruction of the CSC, and wherein the antibody is conjugated to a cytotoxic or chemotherapeutic agent.

4. The method of claim 3, wherein the myoproliferative disorder is an acute myeloid leukemia (AML) or chronic myeloid leukemia (CML) cell.

5. The method of claim 3, wherein the pharmaceutical composition is formulated for parenteral administration.

6. The method of claim 3, wherein the antibody is used adjunctively with an additional chemotherapeutic agent.

7. The method of claim 3, further comprising determining the level of IL1RAP expression before administering.

8. The method of claim 3, further comprising monitoring the level of IL1RAP expression throughout treatment.

9. The method of claim 3, wherein the antibody is administered at a dose of 0.1-10 mg/kg body weight.

10. A method of destroying a human myeloid cancer stem cell (CSC) comprising contacting the CSC with an antibody specific interleukin 1 receptor accessory protein (IL1PRAP), wherein binding of the antibody to IL1RAP mediates destruction of the CSC by complement mediated cytolysis or antibody dependent cellular cytotoxicity.

11. A method of treating myoproliferative disorder in a human subject, comprising
    administering a pharmaceutical composition comprising an antibody specific for interleukin 1 receptor accessory protein (IL1RAP) expressed on the surface of a myeloid cancer stem cell (CSC), wherein binding of the antibody to IL1RAP mediates destruction of the (CSC) by complement mediated cytolysis or antibody dependent cellular cytotoxicity.

12. The method of claim 10, wherein the CSC is an acute myeloid leukemia (IL1RAP) or chronic myeloid leukemia (CML) stem cell.

13. The method of claim 11, wherein the CSC is an acute myeloid leukemia (AML) or chronic myeloid leukemia (CML) stem cell.

14. The method of claim 11, wherein the pharmaceutical composition is formulated for parenteral administration.

15. The method of claim 11, wherein the antibody is used adjunctively with an additional chemotherapeutic agent.

16. The method of claim 11, further comprising determining the level of IL1RAP expression before administering.

17. The method of claim 11, further comprising monitoring the level of IL1RAP expression throughout treatment.

18. The method of claim 11, wherein the antibody is administered at a dose of 0.1-10 mg/kg body weight.

* * * * *